(12) United States Patent
Dormady et al.

(10) Patent No.: US 6,461,834 B1
(45) Date of Patent: Oct. 8, 2002

(54) CLOSTRIPAIN CATALYZED AMIDATION OF PEPTIDES

(75) Inventors: Dan Dormady, Omaha; Jay S. Stout, Lincoln; Daniel J. Strydom, Lincoln; Barton Holmquist, Lincoln; Fred W. Wagner, Walton, all of NE (US)

(73) Assignee: Bionebraska, Inc., Lincoln, NE (US)

( * ) Notice: Subject to any disclaimer, the term of this patent is extended or adjusted under 35 U.S.C. 154(b) by 0 days.

(21) Appl. No.: 09/212,663

(22) Filed: Dec. 16, 1998

Related U.S. Application Data
(60) Provisional application No. 60/107,311, filed on Nov. 6, 1998.

(51) Int. Cl.$^7$ .............................. C12P 21/06; C12N 9/52

(52) U.S. Cl. ...................................... 435/68.1; 435/220

(58) Field of Search ................................. 435/68.1, 220

(56) References Cited

U.S. PATENT DOCUMENTS

| | | | |
|---|---|---|---|
| 4,568,640 A | 2/1986 | Rubin | 435/70 |
| 4,709,014 A | 11/1987 | Tamaoki | |
| 5,093,241 A | 3/1992 | Bennett et al. | 435/69.4 |
| 5,202,239 A | 4/1993 | Tarnowski et al. | 435/69.7 |
| 5,252,464 A | 10/1993 | Andersen | 435/68.1 |
| 5,322,930 A | 6/1994 | Tarnowski et al. | 530/350 |
| 5,332,503 A | 7/1994 | Lee et al. | 210/635 |
| 5,393,666 A | 2/1995 | Linnau | 435/183 |
| 5,416,007 A | 5/1995 | Charette et al. | 435/68.1 |
| 5,595,887 A | 1/1997 | Coolidge et al. | 435/69.7 |
| 5,728,543 A | 3/1998 | Dörschug et al. | 435/68.1 |
| 6,051,399 A * | 4/2000 | Stout et al. | 435/69.1 |

FOREIGN PATENT DOCUMENTS

| | | |
|---|---|---|
| CA | 2069199 | 11/1992 |
| EP | 0 324 659 A2 | 7/1989 |
| WO | WO 89/06656 | 7/1989 |
| WO | WO 90/07005 | 6/1990 |
| WO | WO 91/11457 | 8/1991 |
| WO | WO 94 01451 A | 1/1994 |
| WO | WO 95/17510 | 6/1995 |
| WO | WO 95 20039 A | 7/1995 |
| WO | WO 96/17941 A | 6/1996 |

OTHER PUBLICATIONS

Fruton, J.S., "Proteinase–Catalyzed Syntheis of Peptide Bonds"(1982) Adv. Enzymol. Relat. Areas Mol. Biol., vol. 53, pp 239–306.*
Jakubke et al., "Basic Principles of Protease–Catalyzed Peptide Bond Formation" (1985) Angew. Chem. Int. Ed., Engl., 24(2), 85–93.*
Morihara, K., "Using Proteases in Peptide Synthesis" (Jun., 1987) TIBTECH, vol. 5, 164–170.*
Kasche, V., "Proteases in Peptide Synthesis" (1989) in "Proteolytic Enzymes", Begnon et al., Eds., IRL Press, New York, Chapter 7, pp. 125–143.*
Meiwes et al., "Clostripain: Production and Use for Peptide Synthesis", Biomed. Biochem. Acta, 50(10/11), pp. S80–S83, 1991.*
Henriksen et al., "Peptide Amidation by Chemical Protein Engineering. A Combination of Enzymatic and Photochemical Synthesis", J. Am. Chem. Soc., 114(5), pp. 1876–1877, Feb. 1992.*
A. A. Kembhavi et al., "Clostripain: characterization of the active site," Federation of European Biochemical Societies, 283:277–280 (Mar. 1991).
Asamul—Olsen, S. et al., "Carboxypeptidase mediated C—terminal amidation of polypeptide acids", Biomed. Biochim. Acta, 50(10/11):S106–S109 (1991).
Andersen, A., "Enzymatic Synthesis of Arginine Proline Peptide Bonds Using Clostripain as a Catalyst"Peptides Structure and Function, Proceedings of the Ninth American Peptide Symposium, pp 355–358 (1985).
Bongers, J. et al., "Comparison of enzymatic semisyntheses of peptide amides: human growth hormone releasing factor and analogs", Biomed. Biochim. Acta, 50(10/11):S157–S162 (1991).
Bongers, J. et al., "Semisynthesis of human growth hormone—releasing factor by trypsin catalyzed coupling of leucine amide to a C—terminal acid precusor" Int. J. Peptide Protein Res. 40:268–273 (Mar. 1992).
Fortier, G. et al., "Peptide Bond Synthesis By Clostridopeptidase B", Biotechnology Letters, 8(11):777–782 (Sep. 1986).
Fortier, G. et al., "Substrate—and Stereo—Specification in Clostripain—Catalyzed Peptide Synthesis", Biotechnology Letters, 8(12):873–876 (Oct. 1986).
Fortier, G. et al., "Kinetic Study of Nucleophile Specificity in Dipeptide Synthesis Catalyzed by Clostridopeptidase B", Archives of Biochemistry and Biophysics 276(2):317–321 (Feb. 1990).
Homandberg, G. et al., "Synthesis of Peptide Bonds by Proteinases. Addition of Organic Cosolvents Shifts Peptide Bond Equilibria toward Synthesis", Biochemistry, 17(24):5220–5227 (Jun. 1978).
Homandberg, G. et al., "Enzymatic Conversion of Selected Noncovalent Complexes of Native or Synthetic Fragments to Covalent Forms", Peptides Structure and Biological Function, Proceedings of the Sixth American Peptide Symposium, pp 597–600 (Date Unknown).
Homandberg, G. et al., "Enzymatic Condensation of Non-associated Peptide Fragments Using a Molecular Trap", Biochemistry, 21(14):3385–3389 (1982).

(List continued on next page.)

Primary Examiner—Jon P. Weber
(74) Attorney, Agent, or Firm—Foley & Lardner

(57) ABSTRACT

The invention provides a method of producing a polypeptide having a C-terminal α-carboxamide group. It particularly concerns an enzymatic modification of selected substrate polypeptides which result in cleavage of the substrate polypeptide to form a product peptide with a C-terminal arginine residue having an α-carboxamide group (C-terminal "Arg-NH$_2$"). The method includes contacting an aqueous-based solution including (i) ammonia reagent and (ii) the substrate polypeptide with (iii) clostripain.

25 Claims, 7 Drawing Sheets

OTHER PUBLICATIONS

Jones, R. et al., "The proteinase—catalysed synthesis of peptide hydrazides", *Biochem J.* 203:125–129 (1982).

Juillerat, M. et al., "Clostripain—Catalyzed Re—Formation of a Peptide Bond in a Cytochrome C Fragment Complex", *Int. J. Peptide Protein Res.*, 18:335–342 (May 1981).

Labouesse, B. et al., "Clostripain, protease of *Clostridium histolyticum*. I. Purification and activation by thiols". *Chemical Abstracts* 55: Col. 5615–Col.5616 (1961).

Mitchell, W. et al., "Purification and Properties of Clostridopeptidase B (Clostripain)", *The Journal of Biological Chemistry*, 243(18):4683–4692 (Sep. 25, 1968).

Mitchell, W., "Cleavage at Arginine Residues by Clostripain", *Methods in Enzymology Enzyme Structure Part E*, 47:165–170 (1977).

Proudfoot, A. et al., "A case of spurious product formation during attempted resynthesis of proteins by reverse proteolysis", *Biochem. J.*, 221:325–331 (Apr. 1984).

Ullmann, D. et al., "Kinetic Characterization of Affinity Chromatography Purified Clostripain", *Biol. Chem. Hoppe—Seyler*, 375:89–92 (Feb. 1994).

Witte, V. et al., "Heterologous expression of the clostripain gene from *Clostridium histolyticum* in *Escherichia coli* and *Bacillus subtilis*: maturation of the clostripain precursor is coupled with self—activation", *Microbiology*, 140:1175–1182 (1994).

Yagisawa, S. et al., "Studies on enzymatic condensation of long chain peptides", *Biomed. Biochim. Acta*, 50(10/11):S187–S192 (1991).

Yagisawa, S. et al., "High—efficiency transpeptidation catalysed by clostripain and electrostatic effects in substrate specificity", *Biochem J.*, 266:771–775 (1990).

* cited by examiner

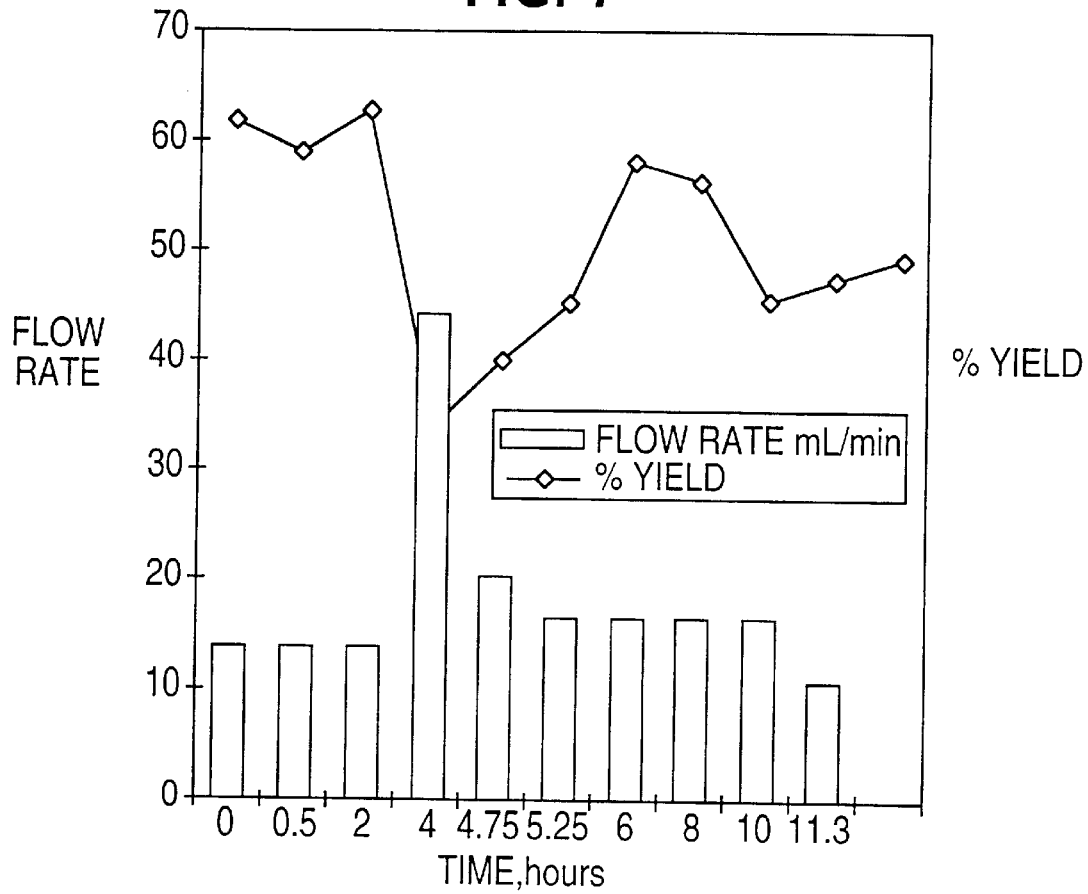

CLOSTRIPAIN CATALYZED AMIDATION OF PEPTIDES

This application claims priority of U.S. Provisional Application No. 60/107,311 filed Nov. 6, 1998.

BACKGROUND OF THE INVENTION

In vitro DNA manipulation allows the transfer of foreign genetic information into a host cell to affect efficient expression of endogenous and foreign proteins in a wide variety of host cells, such as microbial hosts. Recombinant DNA techniques have made possible the selection, amplification and manipulation of expression of proteins and peptides.

Some modifications to a recombinantly produced protein or peptide, however, cannot be accomplished by altering the DNA sequence. Many naturally occurring proteins and peptides contain a C-terminal amino acid residue that has an α-carboxamide group but the amide group is not produced directly through expression. Instead, a precursor protein is produced by genetic expression and the amide is introduced in vivo by enzymatic modification of the precursor protein. In vitro, a variety of methods exist for converting a C-terminal α-carboxylic acid group into an α-carboxamide group, however, the available methods generally have limitations in terms of a number of factors, such as the reaction conditions, selectivity, type of reagent(s) employed and/or types of substrates which may be used.

Moreover, many small foreign proteins and oligopeptides often cannot be successfully overproduced in most cellular hosts, since the host may reassimilate the peptide after expression. For example, where the size of the desired peptide is no more than about 60 to 80 amino acid units in length, degradation rather than end product accumulation usually occurs.

In response to this problem, small peptides have typically been expressed either as part of fusion proteins which include a second larger peptide (e.g., β-galactosidase or chloramphenicol acetyl transferase) or as a recombinant construct which includes multiple copies of the desired peptide (a multicopy construct). In either instance, the initially expressed construct generally needs to be cleaved to produce the desired peptide(s). Very often, the recombinant construct is cleaved to produce a precursor peptide(s) which may then be subjected to posttranslational modification to produce the desired peptide(s). It would be extremely advantageous to have additional method(s) which would allow cleavage of a peptide precursor to be carried out simultaneously with the introduction of an α-carboxamide group into the C-terminal amino acid residue of the cleavage product.

SUMMARY OF THE INVENTION

The invention relates to a method of producing a polypeptide having a C-terminal α-carboxamide group. It particularly concerns an enzymatic modification of selected arginine-containing substrate polypeptides which result in cleavage of the substrate polypeptide to form a product polypeptide having a C-terminal α-carboxamide group. The method includes contacting a substantially aqueous solution which includes (a) the substrate polypeptide ("first polypeptide") and (b) ammonia reagent with (c) clostripain. The substrate polypeptide includes at least one copy of a core amino acid sequence and typically includes more than one copy of the core amino acid sequence (i.e., a multicopy construct). The C-terminal residue of the core amino acid sequence is an arginine residue which is bonded to the adjacent amino acid residue through an α-carboxyl peptide bond (i.e., an "Arg-Xaa" peptide linkage). Since clostripain is an endopeptidase, the Xaa amino acid residue represents an amino acid residue which has its α-carboxylic group bonded to either another amino acid residue through a peptide bond ("Arg-Xaa-Xaa'") or to a carboxyl blocking group ("Arg-Xaa-R"). Carboxyl blocking groups are organic functional groups which replace the acid functionality of the carboxylic acid (the "—OH" portion of the —C(O)OH group) and are capable of being cleaved or hydrolyzed to regenerate a carboxylic acid group ("—C(O)OH group"). Examples of suitable carboxyl blocking groups include groups include the alkoxy portion of an ester group (e.g., the ethoxy or benzyloxy portion of a —C(O)OR group) and the —NRR' portion of a non-peptide amide linkage (e.g., the NRR' portion of a —C(O)NRR' group). The —NRR' portion may be unsubstituted (i.e., $NH_2$) or may be substituted with one or two substituents (e.g., NHEt or $NMe_2$). When such a substrate polypeptide in an aqueous-based solution is contacted with the ammonia reagent in the presence of clostripain, the substrate polypeptide is cleaved at the α-carboxyl peptide bond of the arginine residue and a second polypeptide ("product polypeptide") having a C-terminal arginine residue containing an α-carboxamide group ("Arg-$NH_2$" residue) is produced.

As employed herein, the term "ammonia reagent" refers to a reagent which includes "dissolved free ammonia" (i.e., $NH_3$ dissolved in the aqueous solution) and/or is capable of releasing free dissolved ammonia in an aqueous solution under conditions where clostripain will amidatively cleave an arginine-containing peptide. For example, the ammonia reagent may include one or more salts of ammonia in equilibrium with dissolved free ammonia. The relative amounts of free ammonia and the various salts will generally be a function of various parameters well known to those skilled in the art, such as the pH of the solution, the relative concentrations of different anions present in the solution and/or the solubility of particular individual salts of ammonia. Since the $pK_a$ of ammonia ("$NH_3$") is about 9.2 in aqueous solution, a substantial portion of the ammonia reagent will generally be present as free ammonia at pHs of about 9 or above. In solutions with a pH above the $pK_a$ of ammonia, more than half of the ammonia will generally be present either as dissolved free ammonia or as ammonium hydroxide ("$NH_4OH$"). It also will be understood that the anion portion of a salt of ammonia generally undergoes a very rapid exchange with other anions present in a given solution. Thus, if a pH 10.0 aqueous solution includes chloride salt(s) ("$Cl^-$"), acetate salt(s) ("$OAc^-$") and sulfate salt(s) ("$SO_4^{2-}$"), ammonia reagent in this solution will likely include ammonium chloride ("$NH_4Cl$"), ammonium acetate ("$NH_4OAc$") and ammonium sulfate ("$(NH_4)_2SO_4$"), as well as dissolved free ammonia and ammonium hydroxide ("$NH_4OH$"). The present method typically employs the aqueous-based reaction medium which includes at least about 0.5 M ammonia reagent. It appears that a concentration of ammonia reagent of about 0.75 M to about 1.5 M strikes a balance between optimizing the rate and yield of amidated product formation while avoiding substantial inhibition of the enzyme activity. As employed herein, the concentration of ammonia reagent is based on the equivalents of free dissolved $NH_3$ that are present in the medium. One embodiment of the present method includes forming a solution of the substrate polypeptide in a first aqueous-based medium having a pH of no more than about 8.5 and, preferably having a substantially neutral pH. The substrate polypeptide may be cleaved at the α-carboxyl peptide bond to produce the product polypeptide having a C-terminal Arg-NH$_2$ residue by adjusting the pH of the solution to at least about 9.0 and, typically between about 9.0 to about 11.0, and contacting the substrate polypeptide with an immobilized form of clostripain ("immobilized clostripain") in the presence of ammonia reagent. The substrate and ammonia reagent are preferably contacted with the immobilized clostripain for no more than about 20 minutes and, more preferably, for no more than about 5 minutes.

Typically, the first aqueous-based medium is mixed with a basic aqueous solution ("alkaline medium") to raise the pH shortly before the substrate polypeptide and ammonia reagent are brought into contact with the immobilized clostripain. One manner of practicing this embodiment of the invention is to pack resin containing immobilized clostripain in a chromatography column. The substrate stock solution and basic solutions are mixed just prior to introduction to the column, thereby minimizing the exposure of the substrate polypeptide to high pH aqueous solution. In a typical embodiment of the invention, the basic aqueous solution includes the ammonia reagent. This is not required, however, as some or all of the ammonia reagent may also be present in the reaction medium prior to raising the pH of the reaction medium to at least about 9.0.

Generally, it is also preferred to adjust the pH of the reaction mixture to a value below about 8.5, and preferably to a substantially neutral pH (e.g., a pH of about 6.5 to about 8.0) shortly after the product polypeptide is removed from contact with the immobilized enzyme. Typically, the pH of the reaction mixture containing the product polypeptide is adjusted to about 8.5 or below as soon as the mixture exits the column containing the resin bed with immobilized clostripain. This decreases the chances of the product polypeptide being degraded under the relatively high pH aqueous conditions employed for the clostripain catalyzed amidative cleavage. Polypeptides are known to be susceptible to racemization and/or degradation via hydrolysis under high pH aqueous conditions.

It is typically advantageous to choose the conditions under which the substrate polypeptide is contacted with the immobilized clostripain in the presence of ammonia reagent so as to minimize the amount of time that the substrate and product are subjected to high pH conditions. The present method can be conducted in a manner allows a high yield conversion of substrate to amidative cleavage product while limiting the time the substrate/product solution is in contact with the immobilized enzyme at a pH greater than about 8.5 to no more than about 30 minutes. Preferably, the amidative cleavage is conducted in such a manner that the substrate/product solution is at a pH of 8.5 or above for no longer than about 20 minutes and, more preferably, no longer than about 5 minutes (e.g., the cleavage reaction is carried out in about 2–5 minutes).

BRIEF DESCRIPTION OF THE DRAWINGS

FIG. 7 shows a schematic representation of an apparatus for carrying out an enzymatic amidation of an Arg-containing peptide using immobilized clostripain.

DETAILED DESCRIPTION OF THE INVENTION

Figure 1:
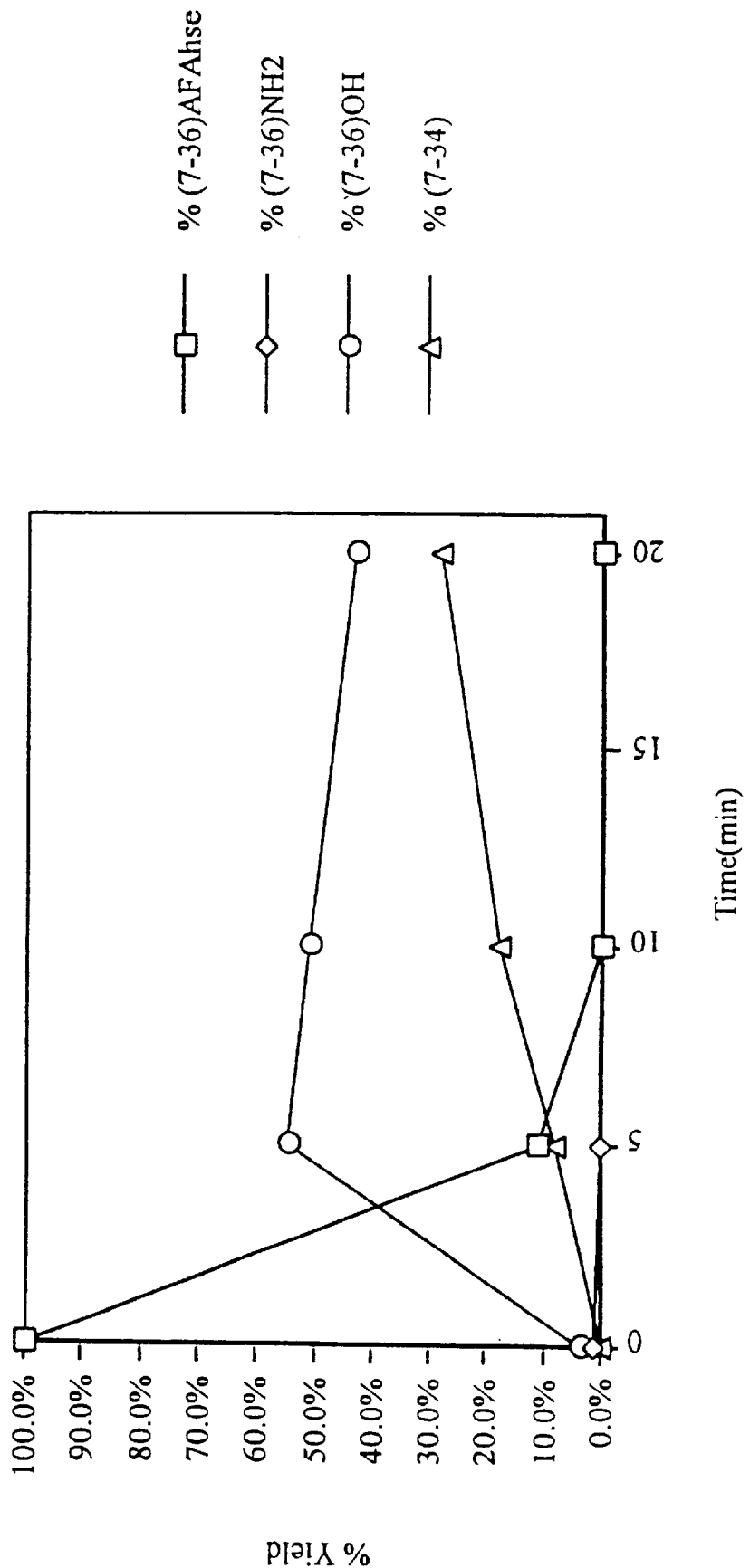
FIG. 1 shows a graph of the relative amounts of starting material and products as a function of time for the clostripain catalyzed amidation of glucagon-like peptide-1 (GLP-1) (7–36)Ala-Phe-Ala-Hse (SEQ ID NO:1) at 37° C. in 1 M NH$_4$OH, 2.5 mM DTT, 1 mM CaCl$_2$ at pH 7.9.

The present method allows the amidative cleavage of a substrate peptide containing an arginine residue to form a product peptide that has a C-terminal arginine residue which has an α-carboxamide group ("C-terminal Arg-NH$_2$"). The method includes contacting the substrate peptide with ammonia reagent in a substantially aqueous solution in the presence of clostripain. The enzyme may be present in either soluble or immobilized form.

As employed herein, the term "clostripain" refers to both native varieties of the enzyme and modified versions thereof. The modified versions retain the functional capability of clostripain to cleave arginine containing peptides amidatively at an Arg-Xaa peptide bond. Examples of suitably modified clostripains include functional mutants which differ from a native clostripain by the substitution, deletion and/or addition of one or more amino acid residues. Other examples of suitably modified versions of clostripain include polypeptides representing a functional fragment of a clostripain which retain the ability to cleave an arginine-containing peptide amidatively, e.g., a functionally active fragment of a native clostripain generated by removing a number of amino acid residues from the amino- and/or carboxyl-terminus of the one or more of the constituent subunits of the enzyme.

Native clostripain (clostridopeptidase B) is an extracellular thiol endoprotease from Clostridia. This protease is a heterodimer and is not homologous with other known thiol proteases. This enzyme is reported to have a molecular weight of about 30,000 to 80,000 and typically has an isoelectric point (pI) of about 4.8 to 4.9. Clostripain was first isolated from a culture filtrate of *Clostridium histolyticum* (Mitchell et al., *J. Biol. Chem.*, 243(18):4683–2602 (1968)). The enzyme is distinguished by a high specificity for Arg-Xaa peptide linkages (especially Arg-Pro linkages) and has both proteolytic and amidase/esterase activity. For example, in the isolated B chain of insulin, clostripain cleaves the Arg-Gly linkage 500 times more rapidly than the Lys-Ala linkage and in glucagon cleavage occurs only at the Arg-Arg, Arg-Ala, and Lys-Try bonds. The relative initial rates of hydrolysis of these three bonds are 1, 1/7 and 1/300 (Labouesse, *Soc. Chem. Biol*, 42:1293 (1960)).

The activity of clostripain is known to be modulated by a variety of activators and inhibitors. Examples of activators of clostripain include calcium ions and mercaptans such as cysteine, 2-mercaptoethanol, and dithiothreitol. Clostripain is also known to be inhibited in the presence of tosyl-L-lysine chloromethyl ketone, hydrogen peroxide, $Co^{2+}$, $Cu^{2+}$, $Hg^{2+}$ or $Cd^{2+}$ ions, EDTA, or citrate.

Clostripain may be prepared by fermentation using microorganisms, e.g., using the method described in U.S. Pat. No. 5,728,543, the disclosure of which is herein incorporated by reference. In this process, Clostridia are cultivated until clostripain accumulates in the nutrient medium. Suitable examples are strains of Clostridia such as *Clostridium histolyticum* DSM 627. Mutants and variants of Clostridia are also suitable as long as the microorganisms are capable of synthesizing clostripain.

Culturing is typically carried out anaerobically, singly or in mixed culture, for example submerged in non-agitated culture in the absence of oxygen or in fermentors, where appropriate, under an atmosphere of an inert gas such as nitrogen. The fermentation is generally carried out in a temperature range from about 25° C. to 40° C. and a pH between 5 and 8.5. The culture broth generally shows a detectable accumulation of the enzyme after 1 to 3 days. The synthesis of clostripain starts in the late log growth phase and reaches its maximum in the stationary growth phase. The production of the enzyme can be followed by means of activity assays (see, e.g., Mitchell, *Meth. Enzym.*: 47: 165–170 (1997)). Although the optimal fermentation conditions differ for each microorganism, suitable conditions are either already known to the person skilled in the art or may be easily established in preliminary tests. Clostripain can be isolated from culture filtrate and purified by classical processes, for example by methanol or ammonium sulfate precipitation, ion exchange or gel permeation chromatography. Recombinantly produced forms of the enzyme are also known (see, e.g., Witte et al., *Microbiology*, 140(5), 1175–1182 (1994)) and may be employed in the present method as long as such enzymes are capable of selective amidative cleavage at Arg-Xaa peptide linkages.

Clostripain is typically activated prior to being employed in the present amidative cleavage reaction by treatment with a reducing agent, such as a mercaptan (a compound which includes a thiol functional group ("—SH")). Examples of suitable reducing agents include mercaptans such as dithiothreitol ("DTT"), dithioerythritol ("DTE"), 2-mercaptoethanol, thioglycolic acid, cysteine and the like. The concentration of mercaptan used to activate the clostripain can be varied over a wide range, e.g., between about 0.05 mM and about 100 mM. Preferably, the present activation of the enzyme for the amidative cleavage reaction is carried out in an aqueous solution which includes about 0.1 to about 5 mM of mercaptan (e.g. DTT). The enzyme activated in this way and/or via the addition of a source of calcium ions as described below can either be used directly or, where appropriate, be freed of activation buffer, such as by chromatography or dialysis.

Since clostripain is also activated by calcium ions ($Ca^{2+}$ ions), the aqueous solutions containing the clostripain employed in the amidative cleavage reaction typically contain a source of $Ca^{2+}$ ions, such as $CaCl_2$. For example, the clostripain is generally employed as an aqueous solution which includes about 0.01 to about 2 mM $CaCl_2$. As indicated above, however, the clostripain may be activated by exposure to $Ca^{2+}$ ions prior to use in the present method.

In this application, standard single letter and three letter abbreviations for amino acid residues (see 37 C.F.R. 1.822) are used. The abbreviation "Hse" refers to homoserine lactone and/or homoserine. This represents a mixture of two forms of an amino acid residue which may be produced by the reaction of cyanogen bromide with a methionine residue, e.g., in the cyanogen bromide cleavage of peptides. The two forms, homoserine and its lactone, exist as a mixture of equilibrium products. The relative amounts of the two forms will vary as a function of pH, with the free acid (homoserine) form being favored at higher pH.

While the aqueous medium used to carry out the amidative cleavage reaction is predominantly composed of water, the medium may include some water-miscible organic solvent. Examples of suitable water-miscible organic solvents include alcohols (such as methanol, ethanol, 1,4-butanediol and trifluoroethanol), ketones, urea, amides (such as N,N-dimethylformamide ("DMF"), N,N-dimethylacetamide ("DMA"), and N-methylpyrolidinone ("NMP")), carbonates (such as propylene carbonate) and ethers (such as tetrahydrofuran) and acetonitrile. While the aqueous medium generally contains no more than about 20% (v/v) organic solvent (i.e., 20 vol. % organic solvent), it has been observed that the presence of organic solvent in the aqueous medium tends to enhance the proteolytic activity of clostripain while decreasing its amidative activity. Accordingly, the present amidative cleavage reaction is typically carried out in an aqueous medium which includes no more than a relatively low level of organic solvent. Typically, the aqueous reaction medium includes no more than about 10% (v/v) and more preferably no more than about 5% (v/v) organic solvent. While the most favorable ratio of amidative activity to proteolytic activity of clostripain is typically observed in aqueous media which are substantially free of organic solvent, i.e., the solution contains no more than about 1% (v/v) of organic solvent, in many instances it may be advantageous to include a small amount of organic solvent in the medium. Examples of particularly suitable organic solvents which may be included in the aqueous medium include propylene carbonate, acetonitrile and ethanol.

Although the temperature of the amidative cleavage reaction can likewise be varied within a wide range, a reaction temperature between about 4° C. and about 80° C. is typically employed. Preferably, the amidative cleavage reaction is carried out at a temperature between 20° C. and 60° C. and a reaction temperature of about 25° C. to about 50° C. is particularly suitable. The present amidative cleavage reaction is typically carried out in an aqueous-based medium having a pH of at least about 9.0. Preferably, the present enzymatically catalyzed amidative cleavage reaction is carried out at between about 9.0 to about 11.0, and the range between about pH 9.5 and pH 10.5 is particularly suitable.

The time required for the amidative cleavage of the substrate polypeptide into the corresponding product polypeptide having a C-terminal Arg-$NH_2$ residue can vary within wide limits depending on the reaction conditions. For example, when conducted using the single-phase solution method, substantial conversion can be accomplished between 15 minutes and 48 hours while a reaction time of between 30 minutes and 6 hours is generally preferred for reasons of convenience. When the amidative cleavage is carried out by contacting the substrate and ammonia reagent with immobilized clostripain, conditions can be chosen to allow substantial conversion (e.g., 40% or higher conversion) of the substrate in about 5 minutes or less. As is known to those skilled in the art, the rate of the reaction can be influenced by a variety of factors including the concentrations of the substrate, ammonia reagent and enzyme, the reaction temperature, the pH of the reaction medium, and the presence or absence of organic solvent in the reaction medium. One or more of such parameters can be adjusted to achieve the desired reaction rate and reaction time.

The relatively high pH conditions typically employed in the amidative cleavage reaction can tend to lead to peptide degradation, e.g., through hydrolytic cleavage reactions and/or isomerization, the latter of which can transform L-amino acid residues into their corresponding D-isomers ("D-contaminants"). It has been found that the rate of degradation is influenced by the reaction medium including salts, solvents and the like as well as the temperature and pH of the reaction medium. For example, when a pH 10.5 aqueous solution of GLP-1(7–36)$NH_2$ (SEQ ID NO:4) containing 1 M $NH_4OH$ was allowed to stand at 45° C. for 44 hours, a substantial amount of the peptide was degraded into D-contaminants. Substantially less degradation (8% D-contaminants) was detected when a similar solution was allowed to stand at 44° C. for 44 hours at neutral pH and essentially no degradation was observed with similar solutions allowed to stand for a similar time period at −20° C. and 4° C.

In contrast, when solutions of GLP-1(7–36)$NH_2$ (SEQ ID NO:4) dissolved at pH values between about 4 to 8.4 in water were allowed to stand at temperatures ranging from −20° C. to 45° C. for a similar period of time, essentially no formation of D-contaminants was detected. Additional experiments examining the degradation of GLP-1(7–36) $NH_2$ (SEQ ID NO:4) in 1 M ammonium chloride solutions at a number of pHs ranging from 8.4 to 10.5 (over 25 hours at 45° C.) demonstrated that the peptide was relatively stable at pH 8.4. Substantial degradation (9%) was measured at pH 9.4 under these conditions and increasingly higher rates of degradation were detected with increasingly higher pH. These results suggest that the exposure of the amidated peptide product to relatively high pH (e.g., pH≧9.5) should be minimized to avoid substantial degradation of the substrate and the amidated product.

The effect of varying the concentration of salts of ammonia (ammonia reagent), $NH_4X$, where X is the counter ion for the ammonium ion, such as for example hydroxide, chloride, acetate, or sulfate, on the clostripain catalyzed amidative cleavage was also examined at constant pH and temperature (pH 10.0, 45° C.). Increasing the $NH_4Cl$/ $NH_4OH$ concentration (formed by adjusting the pH of an aqueous $NH_4OH$ solution to 10.0 with hydrochloric acid) from 0.5 M to 1.0 M led to an increase in the rate of formation and yield of the desired amidative cleavage product without substantially increasing the amount of D-contaminants that form at relatively high pH. $NH_4OH$ is used here to indicate the hydroxide salt of ammonia. This is produced, e.g., in the commercial form of ammonium hydroxide, by dissolving ammonia in water, and exists in equilibrium with the hydrate of $NH_3$ dissolved in water. In other words, ammonium hydroxide is a mixture of $NH_4^+$ $OH^-$ in equilibrium with "free dissolved $NH_3$." Further increases in the $NH_4Cl$/$NH_4OH$ concentration (to about 2 M) did not provide any substantial increase in maximum yield of the amidated product or in the amount of degradation products. The higher $NH_4Cl$/$NH_4OH$ concentrations did, however, appear to inhibit the activity of the enzyme as the time required to reach maximum yield of the amidated product was almost tripled by increasing the $NH_4Cl$/$NH_4OH$ concentration from 1.0 M to 2.0 M. It thus appears that a $NH_4Cl$/$NH_4OH$ concentration of about 1.0 M (e.g., from about 0.75 M to about 1.25 M) strikes a balance between optimizing the rate and yield of amidated product formation while avoiding substantial inhibition of the enzyme activity. It may be possible to find variants of clostripain which are less sensitive to pH and more active in solutions having a pH above about 10. Further, other counterions of the ammonium ion, e.g., sulfate, chloride are suitable for the amidation and by inference the counterions are not limited to these ions. Typically, due to solution equilibrium reactions, the ammonia reagent will exist as a mixture of $NH_4OH$, one or more other salts of ammonia (e.g., $NH_4Cl$ and/or $NH_4OAc$) and free dissolved $NH_3$.

In an alternative embodiment of the invention, the amidative cleavage reaction can be conducted in a continuous mode, such as by contacting an aqueous solution including the reactants (substrate peptide and ammonia reagent) with a suspension or bed of resin containing immobilized clostripain. Clostripain can be coupled to an immobilization support by a variety of conventional methods. For example, preparations of clostripain, immobilized through reaction with tresyl or aldehyde groups on agarose gels or methacrylate-based resins, or with CNBr-activated agarose have been prepared. Resins prepared in this manner can have widely varying amounts of attached enzyme. Typical resins suitable for use in the present method contain about 0.1 to about 10 mg/mL and, preferably, about 1 to about 5 mg/mL immobilized clostripain. These preparations were very active in amidatively cleaving substrates, such as cleaving polypeptides which include the sequence GLP-1(7–35)-Arg-Ala-Phe-Ala (SEQ ID NO:23) to a polypeptide having a C-terminal GLP-1(7–35)-Arg-$NH_2$ (SEQ ID NO:4) in the presence of ammonia at pH 10. Yields are typically >40%, similar to that observed with the single-phase solution reactions. The resins containing immobilized clostripain can be packed in columns and can act as very efficient catalysts for the amidative cleavage reaction.

The reaction using immobilized clostripain is generally carried out by pumping the peptide substrate in the appropriate aqueous ammonia solution through the column. This obviates the need to remove the potentially troublesome clostripain from the reaction product. The resin bound clostripain can be activated by mercaptans prior to the reaction or the reducing agent can be present during the amidation. Typically, the enzyme is maintained in an activated state by simply including a mercaptan (such as DTT) and calcium salt (such as $CaCl_2$) in the reaction medium. The immobilized enzyme reactor-based amidation also enables a method to minimize exposure of the peptide to high pH conditions which can lead to degradation of the product, specifically to minimize D-contaminant formation and side chain deamidation. For example, two flow-streams, one containing peptide at a relatively low pH where it is stable (e.g., no more than about pH 8.5), and one of appropriate constitution to provide the final pH and chemical conditions for the reaction, may be mixed just prior to introduction of the reaction mixture into the resin bed. The time during which the substrate is in contact with the resin, is typically less than about 20 minutes and preferably no more than about 5 minutes. In addition, immediately on exiting the reactor, the product solution is preferably mixed with an appropriate acid or buffer solution to lower the pH to about 8.5 or below, where the stability of the amidated product is markedly higher.

The present method is useful for producing amidated forms of a variety of peptides which contain a C-terminal arginine residue. The target peptide to be produced may be any useful Arg-terminated polypeptide sequence such as a native sequence, a modified native sequence, a non-native sequence having biological activity, truncated forms thereof and similar versions. The peptides may have a molecular weight of 300 to about 20,000, and generally 400 to 10,000.

Such peptides typically include 3 to 100 amino acids residues, preferably 3 to 70 residues. Examples of such peptides include growth hormone releasing factors, pro-forms of such factors and functional fragments thereof. Suitable examples of substrate peptides that can be transformed into C-terminally amidated peptides using the present method include the following polypeptides:

GLP(1–35)-Arg-Xaa-R (SEQ ID NO:2):
His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Xaa-R
and
GLP-1(7–35)-Arg-Xaa-R (SEQ ID NO:3):
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Xaa-R where R represents a carboxyl blocking group, an amino acid residue, or a peptidyl group (i.e., a sequence of two or more amino acids bonded through α-carboxyl peptide bonds).

The present method may be used to amidatively cleave substrate polypeptides which include more than one copy of the core amino acid sequence. Such multicopy constructs may have adjacent copies directly connected to each other ("contiguously linked"). Very often, however, adjacent copies of the core amino acid sequence are connected by a linker sequence. A linker sequence is a relatively short sequence of amino acids (typically no more than 5 to 10 amino acid residues) which serves as a spacer between adjacent copies of the core amino acid sequence. The amino acid residues of the linker sequence are generally chosen to provide additional sites which may be selectively cleaved by enzymatic or chemical cleavage reagents.

The following examples are presented to illustrate the present invention and to assist one of ordinary skill in making and using the same. The examples are not intended in any way to otherwise limit the scope of the invention.

EXAMPLE 1

Clostripain Catalyzed Amidation at pH 7.9

The substrate peptide, GLP-1(7–36)Ala-Phe-Ala-Hse (SEQ ID NO:1; 2 mg) was dissolved in 900 µL of 1 M aqueous NH$_4$OH and the pH was adjusted to 7.9 using glacial acetic acid. The substrate solution was then incubated at 37° C. for 15 minutes prior to the addition of the clostripain. Clostripain (1 mg) was dissolved in 1 mL of 25 mM dithiothreitol containing 1 mM CaCL$_2$ and allowed to stand at room temperature for 15 minutes. The clostripain solution (100 µL) was added to a test tube containing the substrate solution at 37° C. The tube was closed, mixed by inversion and maintained in a bath at 37° C.

The course of the clostripain catalyzed reaction was monitored by removing 25 µL aliquots of the reaction mixture at time intervals (generally every 5 or 10 minutes). The zero time point was removed from the reaction mixture immediately after the addition of the clostripain stock solution. The reaction aliquots were diluted 10 fold with glacial acetic acid and analyzed by HPLC using a 5 micron C18 reverse-phase column eluted with a shallow linear gradient (to 35% B in 3 min, to 45% B in 6 additional min, then to 100% B by 12.3 min) of the following buffers: A: 95% (v/v) water, 5% (v/v) acetonitrile, 0.1% (v/v) trifluoroacetic acid; B: 5% (v/v) water, 95% (v/v) acetonitrile, 0.1% (v/v) trifluoroacetic acid.

The results (FIG. 1) indicate no significant amidation. Hydrolysis at Arg$_{36}$ to remove Ala-Phe-Ala-Hse (SEQ ID NO:6) without amidation to produce GLP-1(7–36)OH (SEQ ID NO:4) was the primary reaction, with a slight degree of hydrolysis at Lys$_{34}$ to produce GLP-1(7–34)OH (SEQ ID NO:5). The amount of GLP-1(7–36)OH (SEQ ID NO:4) reached a maximum of about 55% (based on starting GLP-1(7–36)Ala-Phe-Ala-Hse) (SEQ ID NO:1) after 5 minutes and then declined due to the slower hydrolytic cleavage at Lys$_{34}$ to produce GLP-1(7–34)OH (SEQ ID NO:5). The cleavage at Lys$_{34}$ indicates that some amount of hydrolytic activity toward this secondary site is present. The significant amount of secondary hydrolytic cleavage observed at Lys$_{34}$ was somewhat unexpected.

GLP(7–36)OH (SEQ ID NO:4):
His-Ala-Glu-Gly-Thr-Phe-Thr-Ser-Asp- Val-Ser-Ser-Tyr-Leu-Glu-Gly-Gln-Ala-Ala-Lys-Glu-Phe-Ile-Ala-Trp-Leu-Val-Lys-Gly-Arg-OH

GLP(7–34)OH (SEQ ID NO:5)
His-Ala-Glu-Gly-Thr-Phe-Thr-Ser-Asp- Val-Ser-Ser-Tyr-Leu-Glu-Gly-Gln-Ala-Ala-Lys-Glu-Phe-Ile-Ala-Trp-Leu-Val-Lys

EXAMPLE 2

Clostripain Catalyzed Amidation at pH 9.0

The clostripain catalyzed amidation of GLP-1(7–36)Ala-Phe-Ala-Hse (SEQ ID NO:1) in 1 M aqueous NH$_4$OH at pH 9.0 and 37° C. was carried out following the procedure and analysis described in Example 1. The pH was adjusted to 9.0 with glacial acetic acid.

Figure 2:
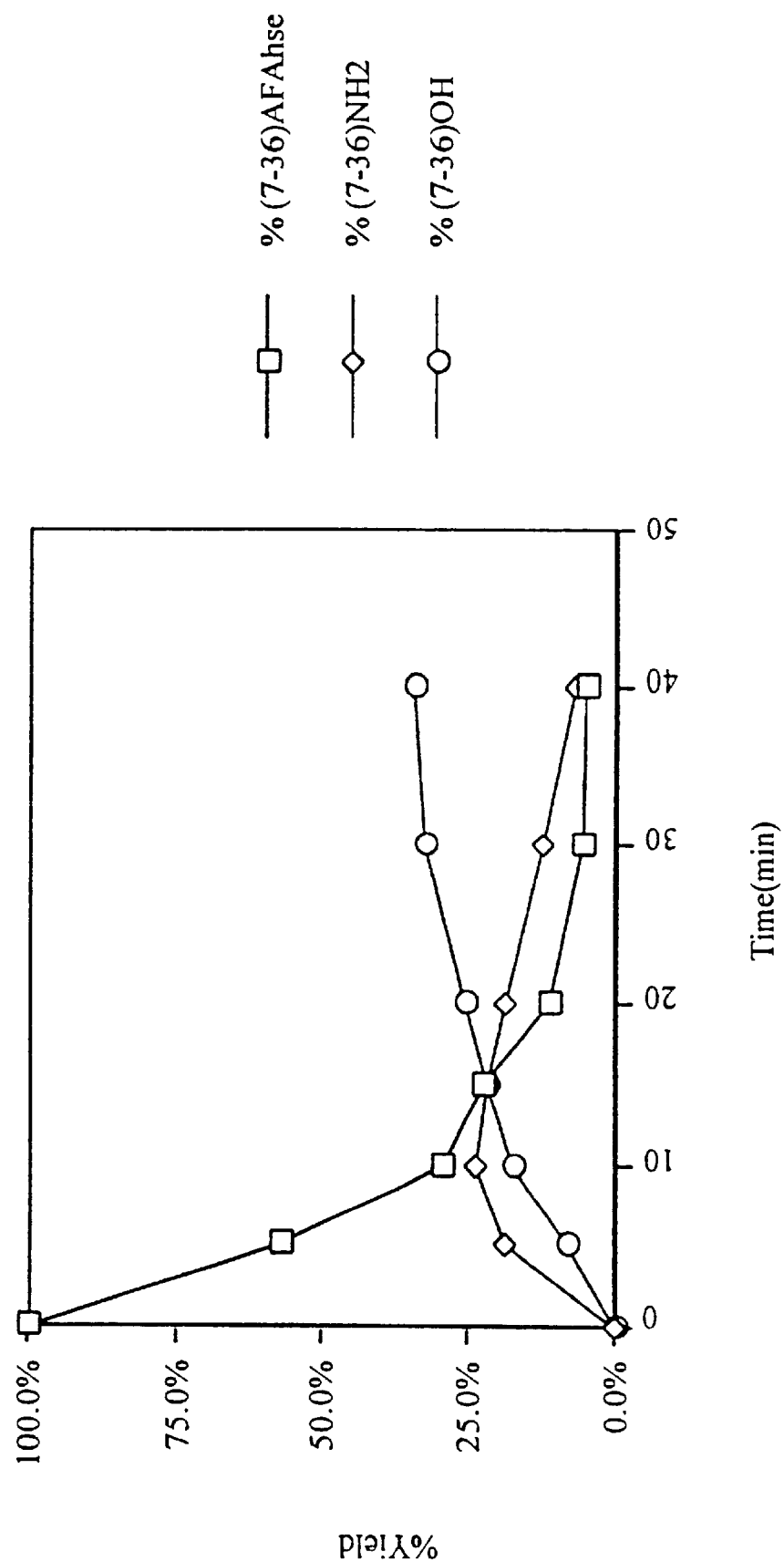
FIG. 2 shows a graph of the relative amounts of starting material and products as a function of time for the clostripain catalyzed amidation of GLP-1(7–36)Ala-Phe-Ala-Hse (SEQ ID NO:1) at 37° C. in 1 M NH$_4$OH, 2.5 mM DTT, 1 mM CaCl$_2$ at pH 9.0.

The results of the reaction performed at pH 9.0 (FIG. 2) indicate a significant amount of amidation producing a maximum yield of 23.6% GLP-1(7–36)NH$_2$ (SEQ ID NO:4) after about 10 minutes. The ratio of amidation to hydrolysis (the ratio of GLP-1(7–36)NH$_2$/GLP-1(7–36)OH) (SEQ ID NO:4) at 10 minutes reaction time was 1.4. At pH 9.0, the hydrolysis at Lys$_{34}$ to produce GLP-1(7–34)OH (SEQ ID NO:5) (not shown) was slower and after 60 minutes only 7.4% was observed.

GLP-1(7–35)-Arg-NH$_2$ (SEQ ID NO:4):
His-Ala-Glu-Gly-Thr-Phe-Thr-Ser-Asp- Val-Ser-Ser-Tyr-Leu-Glu-Gly-Gln-Ala-Ala-Lys-Glu-Phe-Ile-Ala-Trp-Leu- Val-Lys-Gly-Arg-NH$_2$.

EXAMPLE 3

Clostripain Catalyzed Amidation at pH 9.6

The clostripain catalyzed amidation of GLP-1(7–36)Ala-Phe-Ala-Hse (SEQ ID NO:1) in 1 M aqueous NH$_4$OH at pH 9.6 and 37° C. was carried out following the procedure and analysis described in Example 1. The pH was adjusted to 9.6 using glacial acetic acid.

Figure 3:
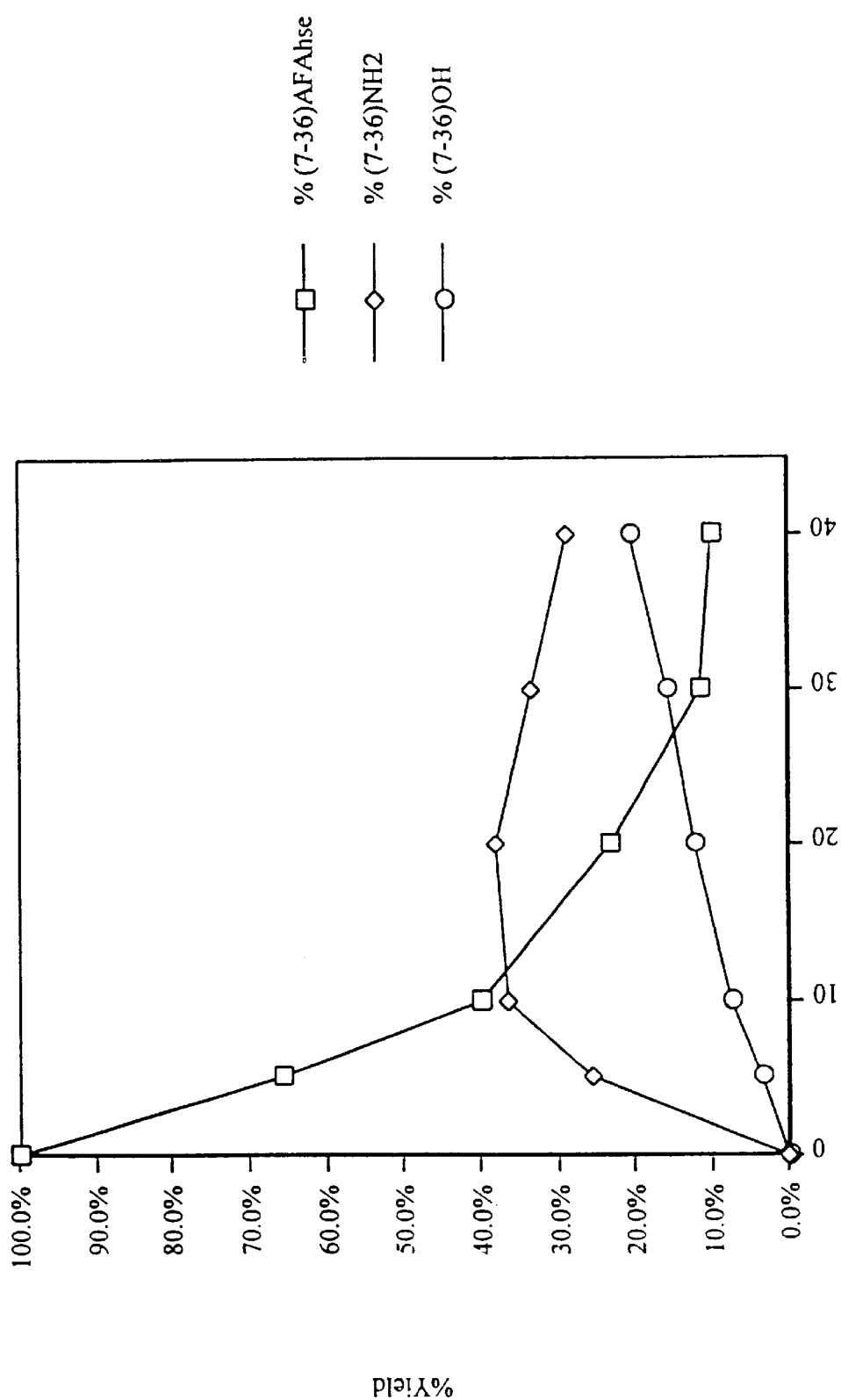
FIG. 3 shows a graph of the relative amounts of starting material and products as a function of time for the clostripain catalyzed amidation of GLP-1(7–36)Ala-Phe-Ala-Hse (SEQ ID NO:1) at 37° C. in 1 M NH$_4$OH, 2.5 mM DTT, 1 mM CaCl$_2$ at pH 9.6.

The results (FIG. 3) show a maximum yield of GLP-1 (7–36)NH$_2$ (SEQ ID NO:4) (38.1%) between 10 and 20 minutes. The ratio of amidation to hydrolysis at 10 minutes was 5.1. The activity of clostripain is slightly lower at pH 9.6 as compared to 9.0 (Example 2), resulting in the maximum yield of GLP-1(7–36)NH$_2$ (SEQ ID NO:4) occurring at a slightly later time.

EXAMPLE 4

Clostripain Catalyzed Amidation at pH 10.4

Figure 4:
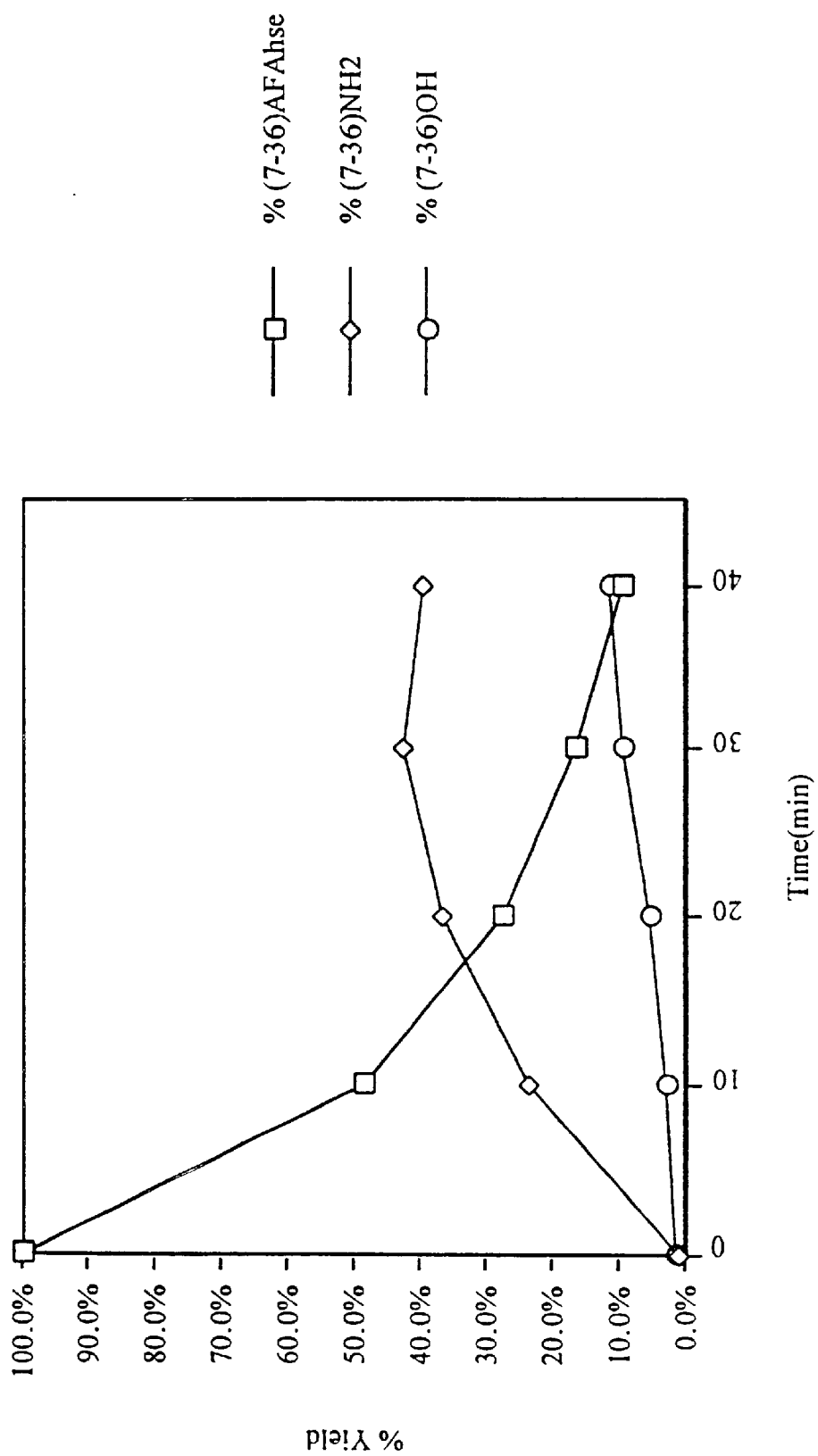
FIG. 4 shows a graph of the relative amounts of starting material and products as a function of time for the clostripain catalyzed amidation of GLP-1(7–36)Ala-Phe-Ala-Hse (SEQ ID NO:1) at 37° C. in 1 M NH$_4$OH, 2.5 mM DTT, 1 mM CaCl$_2$ at pH 10.4.

The clostripain catalyzed amidation of GLP-1(7–36)Ala-Phe-Ala-Hse (SEQ ID NO:1) in 1 M aqueous NH$_4$OH at pH 10.4 and 37° C. was carried out following the procedure and analysis described in Example 1. The pH was adjusted to 10.4 with glacial acetic acid. The results of the attempted amidation at pH 10.4 are shown in FIG. 4. At this pH, the maximum yield of GLP-1(7–36)NH$_2$ (SEQ ID NO:4) (42.3%) was produced after about 30 minutes. The ratio of amidation to hydrolysis at 30 minutes reaction time was 4.7. The yield of GLP-1(7–34)OH (SEQ ID NO:5) after 60 minutes (not shown) was 9.4%, similar to the amount observed at pH 9.0 and 9.6. This demonstrates that at pH 10.4 the amount of hydrolytic cleavage at $Lys_{34}$ is less than that at the lower pH values.

EXAMPLE 5

Clostripain Catalyzed Amidation at pH 11.0

Figure 5:
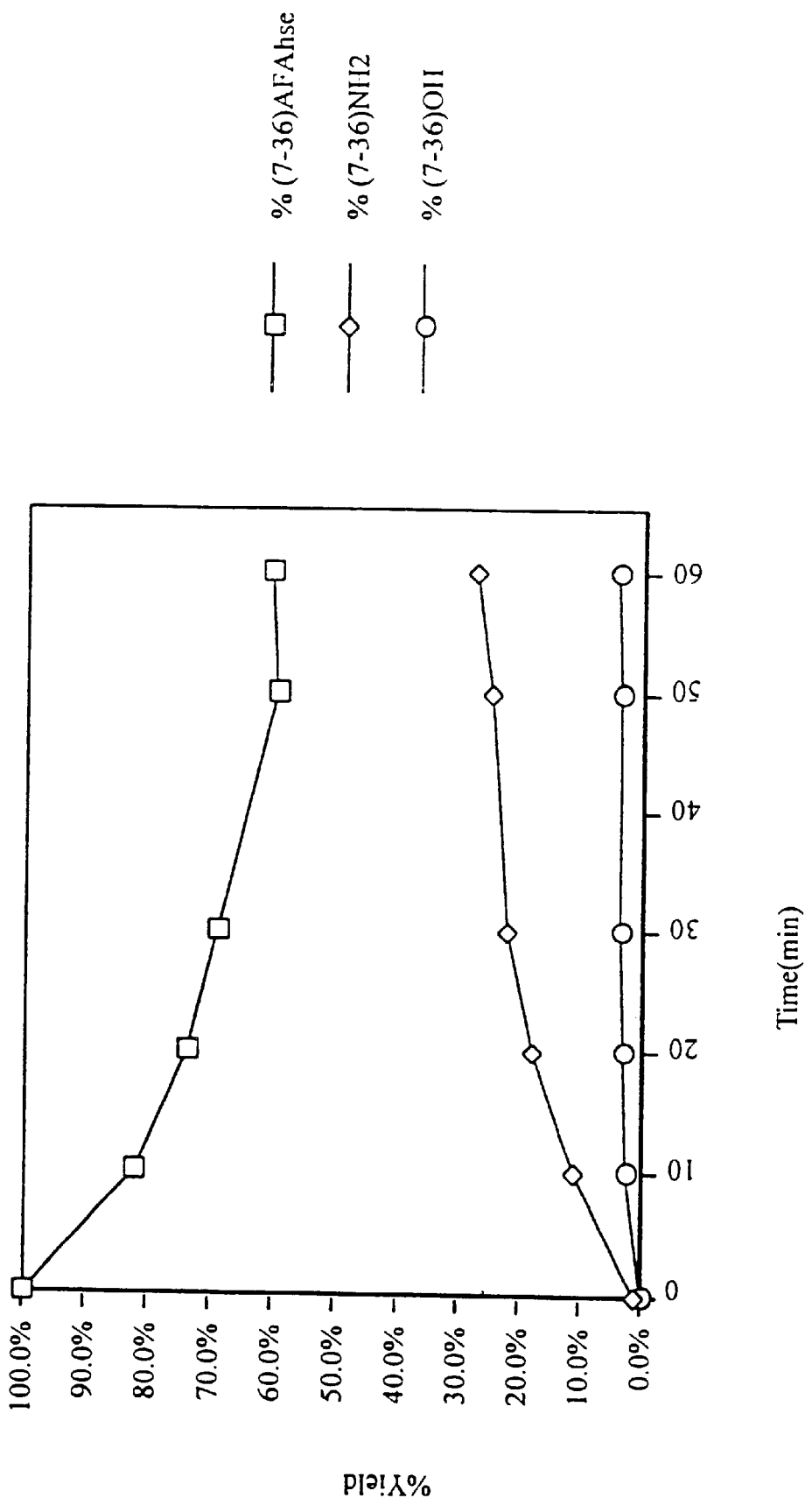
FIG. 5 shows a graph of the relative amounts of starting material and products as a function of time for the clostripain catalyzed amidation of GLP-1(7–36)Ala-Phe-Ala-Hse (SEQ ID NO:1) at 37° C. in 1 M NH$_4$OH, 2.5 mM DTT, 1 mM CaCl$_2$ at pH 11.0.

The clostripain catalyzed amidation of GLP-1(7–36)Ala-Phe-Ala-Hse (SEQ ID NO:1) in 1 M aqueous $NH_4OH$ at pH 11.0 and 37° C. was carried out following the procedure described in Example 1. The pH was adjusted to 11.0 with glacial acetic acid. The results of the attempted amidation at pH 11.0 are shown in FIG. 5. At this pH, a 27.6% yield of GLP-1(7–36)$NH_2$ (SEQ ID NO:4) was obtained after 60 minutes. The ratio of amidation to hydrolysis at 60 minutes reaction time was 7.0. The reaction progressed much more slowly, however, than at any of the lower pH values and had not yet reached a maximum yield after 60 minutes. Amidation is strongly favored over hydrolytic cleavage at this relatively high pH, as even after 60 minutes the GLP-1(7–36)OH (SEQ ID NO:4) yield was increasing at a slower rate than the GLP-1(7–36)$NH_2$ (SEQ ID NO:4) yield. No hydrolysis at $Lys_{34}$ to produce GLP(7–34)OH (SEQ ID NO:5) was observed at this higher pH.

EXAMPLE 6

Clostripain Catalyzed Amidation of GLP-1(7–36)-Ala-Phe-Ala-Met-His-Ala-Glu

The clostripain catalyzed amidation of GLP-1(7–36)Ala-Phe-Ala-Met-His-Ala-Glu (SEQ ID NO:7) was examined in 1 M aqueous $NH_4OH$ and 37° C. following the procedure described in Example 1. The amidation was carried out at pH 10.3 and 10.8 and produced maximum yields of 32.9% and 12.4% GLP-1(7–36)$NH_2$ (SEQ ID NO:4), respectively. Table I shows a comparison of these results with those of the clostripain catalyzed amidation with GLP-1(7–36)Ala-Phe-Ala-Hse (SEQ ID NO:1) as substrate. The results suggest an optimum pH range between about 9.0 and 11.0 and, preferably, between pH 9.5 and 10.5.

TABLE I

Amidation Yield and Selectivity as a Function of pH

| pH | Substrate | Yield GLP-1(7-36)$NH_2$ (%)[a] | Ratio GLP-1(7-36)$NH_2$/ GLP(7-36)$OH$[b] |
|---|---|---|---|
| 7.9 | GLP(7-36)AFAHse (SEQ ID NO: 1) | none | nd |
| 9.0 | GLP(7-36)AFAHse (SEQ ID NO: 1) | 3.6 | 1.4 |
| 9.6 | GLP(7-36)AFAHse (SEQ ID NO: 1) | 38.1 | 3.1 |
| 10.4 | GLP(7-36)AFAHse (SEQ ID NO: 1) | 42.3 | 4.7 |
| 11.0 | GLP(7-36)AFAHse (SEQ ID NO: 1) | 27.6[c] | 7.0 |
| 10.3 | GLP(7-36)AFAHAE (SEQ ID NO: 24) | 32.9 | nd |
| 10.8 | GLP(7-36)AFAHAE (SEQ ID NO: 24) | 12.4 | nd |

[a]Maximum yield;
[b]Ratio at time maximum yield observed;
[c]After 60 minutes (maximum yield not yet attained).

EXAMPLE 7

Amidation of Synthetic Substrates

Synthetic substrates of the generic structure Val-Lys-Gly-Arg-XXXX ("VKGRXXXX"; SEQ ID NO:8)), where "XXXX" represents a peptidyl fragment of three or four amino acid residues, were incubated with clostripain in 1 M ammonium chloride, pH 10.4, 2 mm DTT, 1 mM calcium chloride at 45° C. Aliquots of the reaction mixtures were taken at various time intervals, quenched with glacial acetic acid, and analyzed by capillary electrophoresis. Table II summarizes the percent cleavage of the substrate after 10 minutes at identical clostripain concentrations for the various substrates. The major product in all cases identified by HPLC analysis was the C-terminal α-carboxamide of Val-Lys-Gly-Arg ("VKGR-$NH_2$"; SEQ ID NO:9). Clearly, the nature of the C-terminal fragment can be varied widely and still have considerable capacity to be the object of amidative cleavage.

TABLE II

| Substrate (VKGR-XXXX) "XXXX" | Percent substrate remaining (after 10 min reaction) | SEQ ID NO |
|---|---|---|
| AFFG | 50.7 | 10 |
| AFAM | 56.7 | 11 |
| AFM | 73.1 | 12 |
| APAG | 64.7 | 13 |
| AFAHse | 67 | 6 |
| AFHse | 71 | 14 |
| LAFG | 82.9 | 15 |
| AAGG | 81.9 | 16 |
| ALAG | 78.7 | 17 |
| AAPG | 82.5 | 18 |
| LAAG | 85 | 19 |
| AAFG | 80.8 | 20 |
| QAQG | 90.6 | 21 |
| HAEG | 95.4 | 22 |

EXAMPLE 8

Laboratory Scale Preparation of GLP-1(7–36)$NH_2$ by Amidative Cleavage of GLP-1(7–36)Ala-Phe-Ala-Hse by Clostripain Lyophilized peptide GLP-1(7–36)Ala-Phe-Ala-Hse (SEQ ID NO:1), prepared by recombinant technology, was dissolved at 4.24 mg/mL in 1.16 M $NH_4OH$, 0.25 M HCl, 2.5 mM DTT, 1 mM CaCl adjusted to pH 10.5 with 0.15 M NaOH, and clostripain was added at an enzyme:substrate ratio of 1:300. The reaction was allowed to run for 4.5 hours at 45° C. prior to quenching with 10 mM EDTA. The GLP-1(7–36)$NH_2$ product (SEQ ID NO:4) was purified by chromatography using reversed phase conditions on Amberchrome CG71 and lyophilized.

The product peptide had an amino acid composition identical within experimental error to the theoretical composition of GLP-1(7–36)$NH_2$ (SEQ ID NO:4), had an absorption spectrum which reflected accurately the expected content of tyrosine and tryptophan, had an atomic mass of 3298 measured by MALDI-TOF mass spectrometry (identical within experimental error to that expected), had a sequence identical to the theoretical, and migrated identically to a synthetic commercial sample of the peptide on HPLC, well separated from GLP-1 (7–36)OH (SEQ ID NO:4). The product polypeptide is therefore identified as GLP-1(7–36)$NH_2$ (SEQ ID NO:4).

EXAMPLE 9

Effect of Organic Solvent on Clostripain Proteolytic Activity

A substrate solution (1 mL) of 2 mg N-Bz-Phe-Val-Arg-p-nitroanilide in 2.5 mM dithiothreitol, 1 mM calcium chloride, 50 mM Tricine buffer at pH 8.5 was incubated at room temperature with 10 μg of clostripain, in an aqueous solution containing 10% (v/v) of organic solvent. Initial rates were determined by photometric detection of the liberated p-nitrophenolate anion.

TABLE III

Effect of Organic Solvent on Clostripain Proteolytic Activity.

| Organic Solvent | Activity Relative to Medium Lacking Organic Solvent (% (v/v)) |
|---|---|
| Acetonitrile | 180 |
| Propylene carbonate | 264 |
| Trifluoroethanol | 200 |
| Dimethylformamide | 123 |
| Dimethylacetamide | 108 |
| Tetrahydrofuran | 26 |
| 1,4-Butanediol | 116 |
| N-Methylpyrolidinone | 90 |

These reactions were repeated in the presence of varying amounts of organic solvent, and optimal concentrations for proteolytic activity were determined for propylene carbonate (10%), N,N-dimethylformamide (20%), trifluoroethanol (20%), and acetonitrile (20%).

EXAMPLE 10

Inhibition of Clostripain Amidation Activity by Organic Solvent

Maximal attained amidation level in the presence of various organic solvents was determined with GLP-1(7–36) Ala-Phe-Ala-Hse (SEQ ID NO:1; 2 mg/mL) in 2.5 mM DTT, 1 mM calcium chloride, 2 M ammonium acetate, pH 10.4, at 45° C., with 20 μg clostripain in a 1 mL reaction. Aliquots of the reaction mixture were removed at regular time intervals, quenched with acetic acid and assayed by HPLC analysis on a reverse phase HPLC column.

TABLE IV

Effect of Organic Solvent on Clostripain Amidation Activity.

| Solvent | Extent of amidation (% of substrate converted) |
|---|---|
| Aqueous Control (No organic solvent) | 44 |
| 20% Trifluoroethanol | 9 |
| 10% Propylene carbonate | 29 |
| 20% Acetonitrile | 18 |

The results in Table IV show that a depression of amidation activity was evident in the presence of these solvents. A series of reactions were performed at 1.25 M $NH_4OH$, pH 10.0, 2.5 mM DTT, 1 mM $CaCl_2$, 45° C., at an enzyme to substrate ratio (w/w) of 1:190 at various low concentrations of acetonitrile and ethanol (Table V). Low levels of acetonitrile or ethanol had little effect on transamidation yields, the rates of the reactions, or the ratio of GLP-1(7–36)$NH_2$ (SEQ ID NO:4) to GLP-1(7–36)OH (SEQ ID NO:4), but did decrease the amount of D-contaminants produced.

TABLE V

| Solvent | Max. Yield (%) | Max. Yield (min.) | % D | GLP-1(7-36)$NH_2$/ GLP-1(7-36)OH |
|---|---|---|---|---|
| Water | 60 | 90 | 3.4 | 4.9 |
| 4% Acetonitrile | 57 | 90 | 1 | 3.9 |
| 2% Acetonitrile | 59 | 120 | 1.2 | 4.1 |
| 5% Acetonitrile | 60 | 90 | nd | 5.2 |
| 10% Ethanol | 58 | 150 | nd | 3.3 |
| 5% Ethanol | 59 | 120 | nd | 4.0 |
| 2.5% Ethanol | 62 | 90 | nd | 5.4 |

Abbreviations used:
nd—not determined;
% D—percent D-contaminants.

EXAMPLE 11

Effect of Ammonia Concentration on Transamidation

The effect of variations in ammonia concentrations (0.5, 0.75, 1.0, 1.25, 1.5, and 2 M) at pH 10 on the amidative cleavage of GLP-1(7–36)Ala-Phe-Ala-Hse (SEQ ID NO:1) was examined in the following reaction conditions: 4 mg/mL GLP-1(7–36)Ala-Phe-Ala-Hse (SEQ ID NO:1), 2.5 mM DTT, 1 mM $CaCl_2$, 45° C., enzyme to substrate ratio=1:190. The results are shown in Table VI below. Three ammonia concentrations, 1.0, 1.25, and 1.5 M, gave similar yields (43, 45, and 44% respectively). All yielded the same amount of D-contaminants, 4.2%, and the proportions of each were roughly the same.

TABLE VI

Effect of Ammonia Concentration.

| $NH_4OH$ Conc. (M) | Max Yield[a] (%) | Time[b] (min) | GLP-1(7-36)$NH_2$/ GLP-1(7-36)OH[c] | D-Contaminants[d] (%) |
|---|---|---|---|---|
| 0.5 | 34 | 30 | 1.6:1 | 3.4 |
| 0.75 | 39 | 40 | 2.5:1 | 3.5 |
| 1.0 | 43 | 60 | 4.4:1 | 4.2 |
| 1.25 | 45 | 100 | 5:1 | 4.2 |
| 1.5 | 44 | 140 | 5.6:1 | 4.2 |
| 2.0 | 41 | 165 | 7.5:1 | 4.3 |

[a]Maximum yield of GLP-1(7-36)$NH_2$;
[b]Time when maximum yield obtained;
[c]Ratio of GLP-1(7-36)$NH_2$/GLP-1(7-36)OH at time required to achieve maximum yield;
[d]% D-contaminants due to degradation of product via D-amino acid formation at the time of maximum yield).

EXAMPLE 12

Ammonium Counter Anion Effect on Transamidation

The effect of variations in the counter anion present in the ammonia reagent on transamidation was examined. The reactions were pH adjusted in duplicate, i.e., were run in the presence of ammonium chloride, ammonium acetate, and ammonium sulfate, respectively. Amidative cleavage reactions of GLP-1(7–36)Ala-Phe-Ala-Hse (SEQ ID NO:1; 1.28 mg/mL) in a reaction medium consisting of 2.5 mM DTT, 1 mM $CaCl_2$, 45° C. and an enzyme substrate ratio of 1:190 with 1.25 M $NH_4OH$ adjusted to pH 10.0 with hydrochloric acid, acetic acid or sulfuric acid were run in duplicate.

The results are shown in Table VII below. The yields of product for all reactions were nearly identical as was the amount of D-contaminants and hence, the nature of the counterion appears to have little effect on the amidation to produce GLP-1(7–36)NH$_2$ (SEQ ID NO:4).

TABLE VII

Effect of Ammonium Ion Counterion.

| Counterion | GLP-1(7-36)NH$_2$ Yield[a] | % D-Contaminants[b] |
|---|---|---|
| Cl$^-$ | 51% | 4.7% |
| OAc$^-$ | 51% | 4.8% |
| SO$_4^-$ | 42% | 4.0% |

[a]After 150 minutes, none of the reactions had reached a maximum yield;
[b]% D-contaminants due to degradation of product via D-amino acid formation (at 150 min.).

EXAMPLE 13

Effect of CaCl$_2$ Concentration on Transamidation

Amidative cleavage of GLP-1(7–36)Ala-Phe-Ala-Hse (SEQ ID NO:1; 1 and 5 mg/mL) was examined in reactions containing 0, 0.1, 1.0, and 10 mM CaCl$_2$ (Table VIII) in the presence of 1.25 M NH$_4$OH, adjusted to pH 10.0 with HCl, 2.5 mM DTT, enzyme to substrate ratio=1:200. No activity was observed in the absence of added calcium. Thus, this cation is required for activity and concentrations above 0.1 mM do not affect the yield of transamidation.

TABLE VIII

Effect of CaCl$_2$ Concentration On Amidatitive Cleavage

| CaCl$_2$ Conc. (mM) | Substrate Conc. (mg/mL) | Max. Yield[a] (%) | GLP-1(7-36)NH$_2$/GLP-1(7-36)OH[b] |
|---|---|---|---|
| 0 | 1 | NA | NA |
| 0.1 | 1 | 60 | 4.6:1 |
| 1.0 | 1 | 59 | 4.4:1 |
| 10 | 1 | 59 | 4.4:1 |
| 0 | 5 | 2 | — |
| 2 | 5 | 47 | 4.3:1 |

NA—No activity;
[a]Maximum yield of GLP-1(7-36)NH$_2$;
[b]GLP-1(7-36)NH$_2$/GLP-1(7-36)OH when maximum yield achieved.

EXAMPLE 14

Effect of Enzyme Concentration on Amidative Cleavage

Amidative cleavage of GLP-1(7–36)Ala-Phe-Ala-Hse (SEQ ID NO:1; 1 mg/mL) at enzyme/substrate ratios of 1:200, 1:400, 1:800; and 1:400 was examined at 1.25 M NH$_4$OH, adjusted to pH 10.0 with HCl, 2.5 mM DTT, 0.5 mM CaCl$_2$, at 45° C., under nitrogen (Table IX) and analyzed as in Example 1. Yields of GLP-1(7–36)NH$_2$ (SEQ ID NO:4) were between 50 and 60% in all cases but at the lower enzyme to substrate ratios the time to reach the maximal yield was considerably longer, reaching 360 min at a ratio of 1:800. At the higher substrate concentration the yield was still appreciable though the reaction produced less product and it reached maximal yield at a longer time. As the reaction times increase under high pH conditions the amount of D-contaminants increases, as would be expected since the substrate and product are exposed to the alkaline pH for extended times.

TABLE IX

Enzyme/Substrate Ratio.

| Substrate Conc.[a] (mg/mL) | Enzyme/Substrate Ratio | Max. Yield[b] (%) | (min) | D-Contaminants[c] (%) |
|---|---|---|---|---|
| 1 | 1:200 | 59 | 90 | 3% |
| 1 | 1:400 | 60 | 190 | 4.5% |
| 1 | 1:800 | 58 | 360 | 6% |
| 5 | 1:400 | 51 | 90 | nd |

[a]GLP-1(7-36)Ala-Phe-Ala-Hse (SEQ ID NO: 1).
[b]Maximum yield of GLP-1(7-36)NH$_2$ and the time of its occurrence.
[c]% D-contaminants at the time of maximum yield (due to degradation of product via D-amino acid formation).

EXAMPLE 15

Mercaptan Reduction Required for Clostripain Activity

To obtain maximal activity, clostripain is typically treated with mercaptan. The concentration of the mercaptan, DTT, was examined at 0, 0.5, 1.0, 2.5, and 5.0 mM concentrations. The conditions for the amidative reaction were: 1 mg/mL GLP-1(7–36)Ala-Phe-Ala-Hse (SEQ ID NO:1), 1.25 M NH$_4$OH, adjusted to pH 10.0 with HCl, 0.5mM CaCl$_2$, 45° C., N$_2$(g) sparged headspace, enzyme to substrate ratio= 1:400, and the reaction assayed as in Example 1.

In the absence of added DTT only a 20% yield of amidation product GLP-1(7–36)NH$_2$ (SEQ ID NO:4) was obtained. When run in the presence of from 0.5 to 5 mM all reactions produced about 60% GLP-1(7–36)NH$_2$ (SEQ ID NO:4). Thus, to get optimal yields of amidative cleavage, reduction of the enzyme with a reducing agent such as a mercaptan is required.

EXAMPLE 16

Amidation by Other Arg-specific Proteases

GLP-1(7–36)Ala-Phe-Ala-Hse (SEQ ID NO:1) (between 0.5 and 2 mg/mL) was dissolved in 1 M ammonium hydroxide at pH 10 and 8.5 and incubated individually with six different proteolytic enzymes, five of which have a specificity to cleave peptides at the carboxyl peptide bond of arginine residues, similar to that of clostripain. These included trypsin, thrombin, cathepsin B (also tested at pH 5.5), coagulation factor Xa, plasmin and papain. Papain is a thiol protease, albeit one which is not specific to arginyl bonds. None of these proteases produced any GLP-1(7–36)NH$_2$ (SEQ ID NO:4) as assayed by reversed phase chromatography as described in Example 1. Enzyme:substrate ratios were between 1:50 to 1:100 and protease specific additives were added where appropriate (e.g., calcium chloride). Under these conditions only clostripain produced measureable GLP-1(7–36)NH$_2$ (SEQ ID NO:4).

EXAMPLE 17

Clostripain Affinity Purification

Clostripain was purified by affinity chromatography (Ullman et al., *Biol. Chem. Hoppe-Seyler*, 375, 89–92 (1994)) using a column of Toyopearl TSKgel AF-Red resin packed in a jacketed 1.2 cm ID column at a bed height of 11 cm. Buffer A (25 mM Hepes, 5 mM CaCl$_2$, pH 8) and buffer B (25 mM Hepes, 5 mM CaCl$_2$, 1 M NaCl, pH 8) were filtered through a 0.45 μm nylon filter and degassed by vacuum for ten minutes.

Clostripain (57.3 mg; Worthington) was dissolved at 14.5 mg/mL in 3 mL of 15% buffer B in buffer A and applied to the column that had been preequilibrated with 15% B in buffer A, at 1 mL/minute. The column was eluted with 15% buffer B in buffer A for five minutes then with a linear gradient of from 15% to 100% buffer B in buffer A over forty minutes. Fractions were collected and those containing clostripain, as identified by their ability to catalyze amidation, were pooled and made up to about 5 mM dithiothreitol and concentrated to 5 mg/mL by ultrafiltration.

EXAMPLE 18

Immobilization of Clostripain on Toyopearl AF-Formyl-650M Resin

Toyopearl AF-Formyl-650M Resin, supplied as a slurry containing preservative, was added to a 10 mL disposable column with a 45 um frit, and rinsed with 2 column volumes of 0.1M Mes buffer, 5 mM $CaCl_2$, pH 5. Clostripain from the purification above in 5 mM Hepes, pH 8, was diluted into an equal volume of 0.1 M Mes, to a final pH of 5.5. and added to the drained resin. Sodium cyanoborohydride (150 µL of 1 M) was then added and the resin slurry was mixed by continuous inversion of the capped column for 20 hours at 23–25° C. The column was drained, reserving the eluant for analysis, and the resin washed with 2 column volumes of 1 M Tris-HCl, 5 mM $CaCl_2$, pH 7.8. A column volume of this buffer was then added along with 50 µL of sodium cyanoborohydride and the mixture mixed for 1 hour. The resin was then washed with 10 column volumes of 1 M NaCl, 25 mM Hepes, 5 mM $CaCl_2$ pH 8, then with the same amount of buffer containing no NaCl. Analysis of the resulting clostripain resin preparation by measurement of the loss of enzyme from solution showed that between 1.8 and 4.4 mg of enzyme was coupled per mL of resin. The clostripain resin was stored in this buffer at 4° C. until used.

Similarly, clostripain immobilized on other resins produced similar results. Examples include Toyopearl Amino Link and Toyopearl Formyl 650M (Toso Haas, Inc.) that are aldehyde based resins and Ultra Link (Pierce), an azlactone based resin. These resins bind to free amino groups on the enzyme. All these resins containing immobilized clostripain produced amidative cleavage of GLP-1(7–36)Ala-Phe-Ala-Hse (SEQ ID NO:1) to GLP-1(7–36)$NH_2$ (SEQ ID NO:4) in yields of up to 77%, generally in the 50 to 60% range.

EXAMPLE 19

Immobilized Clostripain Catalyzed Reactions

Immobilized clostripain resin (40 mL) in 50 mM Hepes, 5 mM $CaCl_2$ at pH 8.5 was loaded at 35 mL/min into a 2.5 cm ID glass jacketed column equipped with a flow adapter and a peristaltic pump. Water at 47° C. was circulated through the jacket. The resin was then washed with 200 mL of 1 mM DTT and 1 mM $CaCl_2$ at 47° C. at 8 mL/min at pH 8.5. After column preparation just described the column is then ready for amidative cleavage.

Figure 6:
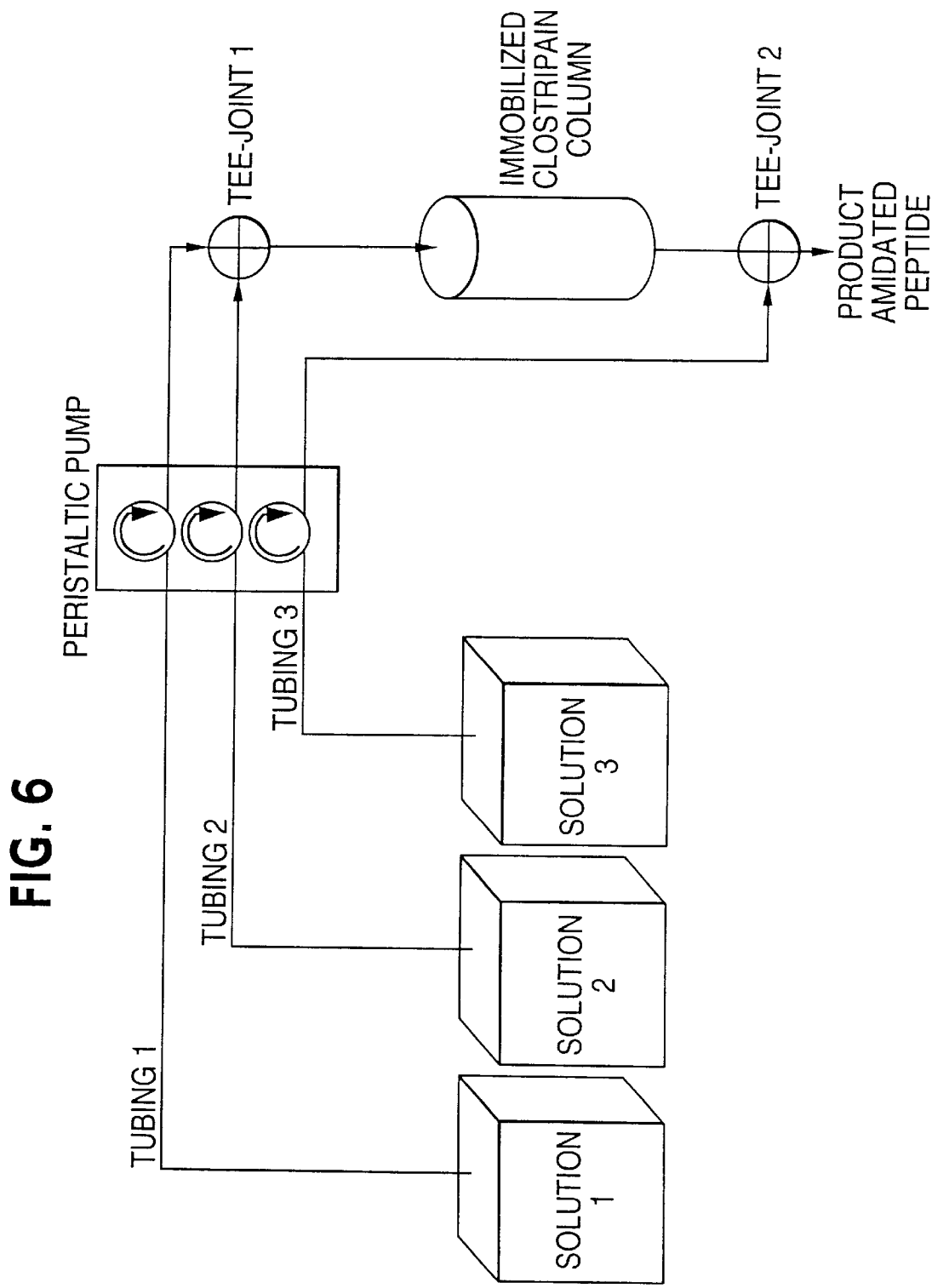
FIG. 6 shows a graph of the yield of GLP-1(7–36)NH2 (SEQ ID NO:4) as a function of flow rate in a clostripain catalyzed amidative cleavage using an immobilized form of the enzyme.

The apparatus diagrammed in FIG. 6 was used for the continuous amidative cleavage of GLP-1(7–36)Ala-Phe-Ala-Hse (SEQ ID NO:1). The substrate solution (13 L at 0.65 mg/mL) in 7.5% aqueous acetonitrile containing 1.25 mM HCl ("Solution 1") was equilibrated in the water bath at 47° C. and connected to the peristaltic pump to Tubing 1 with the outlet of this line connected to Tee-joint 1. A solution of 13 L of 2.5 M $NH_4OH$, 2 mM DTT, and 2 mM $CaCl_2$ was made, adjusted to pH 10.0 with concentrated HCl ("Solution 2"), placed in the 47° C. water bath and connected to the peristaltic pump via Tubing 2 which then is also connected to Tee-joint 1. The third tubing from the pump, Tubing 3, delivers Solution 3 (1.25 M HCl) at room temperature through the pump to the tubing Tee-joint 2 that is connected to the effluent of the column. The outlet of the Tee-joint 2 is collected as the product of the reaction. In practice, the pumping lines of the pump are 0.125 in ID Tygon tubing and the pumping rate of Tubing 1, 2, and 3 are identical at about 3 to 6 mL/min. As Solution 1 and 2 are pumped they meet at Tee-joint 1, they mix forming a mixture at pH 10, and the resulting solution exits Tee-joint 1 and proceeds to the column. This solution passes through the column and enters Tee-joint 2 at a flow rate of about 6 mL/min. At Tee-joint 2, the effluent of the column is mixed with the 1.25 M HCl solution that serves to lower the pH of the reaction solution containing GLP-1(7–36)$NH_2$ (SEQ ID NO:4) to about 8.5. At the flow rate used, the time during which the substrate and product are in contact with the resin is about 5 min. By this manner the time during which the substrate and/or the product are exposed to pH 10 aqueous conditions is no more than about 5 min.

In practice the flow rate is adjusted to achieve maximal product formation and minimal contaminants as assessed by repetitive sampling of the effluent to Tee-joint 2 and HPLC analysis as described in Example 1. FIG. 7 shows the results of this reaction under the conditions described above, where the yield and flow rate of the column are recorded as a function of time for the experiment. The average yield is near 50% for GLP-1(7–36)$NH_2$ (SEQ ID NO:4) formation with a maximum near 64% at a net flow rate at 14 mL/min. When the flow was too rapid, as at 44 mL/min, the yield dropped to 34%. Returning to the flow 16 mL/min brought the yield back up to near 50%.

When product formation is not optimal, the flow is decreased if product formation is low allowing for a longer exposure of the substrate solution to the resin bound clostripain or the flow is increased if overexposure to the enzyme is apparent by increased amounts of GLP-1(7–34) (SEQ ID NO:5) due to cleavage at $Lys_{34}$. It is also understood by anyone skilled in the art that alterations in the neutralizing HCl concentration, the substrate concentration, the temperature, the organic solvent concentration and other factors that effect the rate of immobilized clostripain are variables that can be adjusted to optimize product formation.

EXAMPLE 20

Immobilized Amidated Cleavage: Effect of Column Parameters

A series of reactions with immobilized clostripain on two different resins is shown in Table X where effects of flow rate, GLP-1(7–36)Ala-Phe-Ala-Hse (SEQ ID NO:1) concentration, temperature, resin amount and yield of GLP-1(3–36)$NH_2$ (SEQ ID NO:25) are tabulated for reactions performed analogously to Example 19 and under similar conditions but with 1×15 cm column. Conclusions are that, in general, lowering of the temperature decreases yield (compare first 4 entries at 23° C. with those at 45°) as does significant changing of the flow rates (compare entries 1 and 2, 3 and 4, 6 and 7) and GLP-1(7–36)Ala-Phe-Ala-Hse (SEQ ID NO:1) concentrations. Variations of these and the other parameters of the column reaction can alter the yield. In this study, the yields varied from 4 to 63% depending on the precise conditions used for the reaction, demonstrating that reactions can be optimized by altering the various parameters of the column reaction.

TABLE X

Comparison of Enzyme Reactor Trials

| Base Resin | GLP-1(7-36)-APAHse (mg/mL) | Flow Rate (mL/min) | Yield % | Temp. |
|---|---|---|---|---|
| 1. AminoLink | 0.1 | 1 | 56% | 23° C. |
| 2. AminoLink | 0.14 | 0.1 | 24% | 23° C. |
| 3. AminoLink | 1 | 0.1 | 4% | 23° C. |
| 4. AminoLink | 1 | 4 | 11% | 23° C. |
| 5. AminoLink | 0.14 | 0.5 | 61% | 45° C. |
| 6. AminoLink | 1 | 4 | 48% | 45° C. |
| 7. AminoLink | 1 | 3 | 57% | 45° C. |
| 10. AminoLink | 0.1 | 3 | 63% | 45° C. |
| 11. AminoLink | 0.25 | 2 | 50% | 45° C. |
| 12. Toyopearl Formyl | 0.25 | 2–4 | 60% | 45° C. |
| 13. UltraLink | 0.25 | 1 | 46% | 45° C. |
| 14. Toyopearl Formyl | 0.25 | 2 | 62% | 45° C. |
| 15. Toyopearl Formyl | 0.5 | 2 | 57% | 45° C. |
| 16. Toyopearl Formyl | 1 | 2 | 53% | 45° C. |

The invention has been described with reference to various specific and illustrative embodiments and techniques. However, it should be understood that many variations and modifications may be made while remaining within the spirit and scope of the invention.

---

What is claimed is:

1. A method for producing a polypeptide having a C-terminal α-carboxamide group comprising:

contacting (i) an aqueous-based medium including (a) ammonia reagent, and (b) a substrate polypeptide comprising at least one core amino acid sequence, wherein the core amino acid sequence has a C-terminal Arg residue bonded through its α-carboxyl group to an α-amino group of an adjacent amino acid residue through a peptide bond, with (ii) clostripain to cleave the peptide bond and produce product polypeptide having a C-terminal Arg-NH$_2$ residue.

2. The method of claim 1 wherein the aqueous-based medium includes at least about 80 vol. % water.

3. The method of claim 1 wherein the aqueous-based medium includes no more than about 10 vol. % organic solvent.

4. The method of claim 1 wherein the aqueous-based medium is substantially free of organic solvent.

5. The method of claim 1 wherein the ammonia reagent comprises a salt of ammonia selected from ammonium chloride, ammonium hydroxide, ammonium acetate, ammonium sulfate and mixtures thereof.

6. The method of claim 1 wherein the aqueous-based medium comprises at least about 0.5 M ammonia reagent.

7. The method of claim 1 comprising contacting the substrate polypeptide and the ammonia reagent with clostripain at a temperature of about 4° C. to about 80° C.

8. The method of claim 1 wherein the core amino acid sequence comprises GLP-1(7-35)-Arg-Xaa.

9. The method of claim 8 wherein the core amino acid sequence comprises GLP-1(7-35)Arg-Ala-Phe-Ala (SEQ ID NO:23).

10. The method of claim 9 wherein the core amino acid sequence comprises GLP-1(7-35)Arg-Ala-Phe-Ala-Hse (SEQ ID NO:1) or GLP-1(7–35)Arg-Ala-Phe-Ala-Met-His-Ala-Glu (SEQ ID NO:7).

11. The method of claim 1 wherein the core amino acid sequence comprises a GLP-1(7–35)-Arg-Xaa-R amino acid sequence, where Xaa is an amino acid and R is an α-carboxyl blocking group.

12. The method of claim 1 wherein the substrate polypeptide includes at least two copies of the core amino acid sequence.

13. The method of claim 12 wherein adjacent copies of the core amino acid sequence are connected by a linker sequence.

14. The method of claim 1 comprising contacting the substrate polypeptide and the ammonia reagent with the clostripain in an aqueous-based medium having a pH of about 9.0 to about 11.0.

15. The method of claim 1 wherein the aqueous-based medium further comprises $CaCl_2$.

16. The method of claim 1 wherein the aqueous-based medium further comprises a reducing agent.

17. The method of claim 16 wherein the reducing agent comprises a mercaptan.

18. The method of claim 17 wherein the mercaptan is selected from the group consisting of dithiothreitol, dithioerythritol, 2-mercaptoethanol, thioglycolic acid, cysteine, glutathione, and mixtures thereof.

19. The method of claim 1 wherein the clostripain is an immobilized form of clostripain.

20. A method of producing a polypeptide having a C-terminal α-carboxamide group comprising:

providing a first aqueous-based medium including a substrate polypeptide comprising at least one core amino acid sequence, wherein the core amino acid sequence has a C-terminal Arg residue bonded to an adjacent amino acid residue through an α-carboxyl peptide bond;

mixing the first aqueous-based medium with alkaline medium including ammonia reagent to form a second aqueous-based medium having a pH of at least about 9.0; and contacting the second aqueous-based medium with immobilized clostripain to cleave the substrate polypeptide at the α-carboxyl peptide bond and produce a product aqueous-based medium which includes product polypeptide having a C-terminal Arg-NH$_2$ residue.

21. The method of claim 20 wherein the second aqueous-based medium has a pH of about 9.0 to about 11.0.

22. The method of claim 20 further comprising pH adjusting the product aqueous-based medium to form a third aqueous-based medium including the product polypeptide and having a pH of no more than about 8.5.

23. The method of claim 22 wherein the contacting step comprises contacting the second aqueous-based medium with the immobilized clostripain for no more than about 20 minutes.

24. The method of claim 20 wherein the core amino acid sequence comprises GLP-1(7–35)-Arg-Xaa.

25. The method of claim 20 further comprising activating immobilized clostripain with a mercaptan, $CaCl_2$ or a mixture thereof to form activated immobilized clostripain; and the contacting step comprises contacting the second aqueous-based medium with the activated immobilized clostripain.

* * * * *

SEQUENCE LISTING

<160> NUMBER OF SEQ ID NOS: 25

<210> SEQ ID NO 1
<211> LENGTH: 34
<212> TYPE: PRT
<213> ORGANISM: Escherichia coli
<220> FEATURE:
<221> NAME/KEY: MOD_RES
<222> LOCATION: (34)
<223> OTHER INFORMATION: Xaa is homoserine lactone and/or homoserine

<400> SEQUENCE: 1

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Ala Phe
            20                  25                  30

Ala Xaa

<210> SEQ ID NO 2
<211> LENGTH: 37
<212> TYPE: PRT
<213> ORGANISM: Escherichia coli
<220> FEATURE:
<221> NAME/KEY: VARIANT
<222> LOCATION: (37)
<223> OTHER INFORMATION: Xaa is any amino acid

<400> SEQUENCE: 2

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
            20                  25                  30

Val Lys Gly Arg Xaa
        35

<210> SEQ ID NO 3
<211> LENGTH: 31
<212> TYPE: PRT
<213> ORGANISM: Escherichia coli
<220> FEATURE:
<221> NAME/KEY: VARIANT
<222> LOCATION: (31)
<223> OTHER INFORMATION: Xaa is any amino acid

```
<400> SEQUENCE: 3

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Xaa
             20                  25                  30

<210> SEQ ID NO 4
<211> LENGTH: 30
<212> TYPE: PRT
<213> ORGANISM: Escherichia coli

<400> SEQUENCE: 4

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg
             20                  25                  30

<210> SEQ ID NO 5
<211> LENGTH: 28
<212> TYPE: PRT
<213> ORGANISM: Escherichia coli

<400> SEQUENCE: 5

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys
             20                  25

<210> SEQ ID NO 6
<211> LENGTH: 4
<212> TYPE: PRT
<213> ORGANISM: Artificial Sequence
<220> FEATURE:
<221> NAME/KEY: MOD_RES
<222> LOCATION: (4)
<223> OTHER INFORMATION: Xaa is homoserine lactone and/or homoserine
<223> OTHER INFORMATION: Description of Artificial Sequence: Peptidyl
      fragment

<400> SEQUENCE: 6

Ala Phe Ala Xaa
  1

<210> SEQ ID NO 7
<211> LENGTH: 37
<212> TYPE: PRT
<213> ORGANISM: Escherichia coli

<400> SEQUENCE: 7

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Ala Phe
             20                  25                  30

Ala Met His Ala Glu
         35

<210> SEQ ID NO 8
<211> LENGTH: 8
<212> TYPE: PRT
<213> ORGANISM: Artificial Sequence
<220> FEATURE:
<221> NAME/KEY: VARIANT
<222> LOCATION: (5)..(8)
```

-continued

```
<223> OTHER INFORMATION: Xaa represents a peptidyl fragment of amino
      acid residues
<223> OTHER INFORMATION: Description of Artificial Sequence: Synthetic
      substrate

<400> SEQUENCE: 8

Val Lys Gly Arg Xaa Xaa Xaa Xaa
  1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      substrate

<400> SEQUENCE: 9

Val Lys Gly Arg
  1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Peptidyl
      fragment

<400> SEQUENCE: 10

Ala Phe Phe Gly
  1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Peptidyl
      fragment

<400> SEQUENCE: 11

Ala Phe Ala Met
  1

<210> SEQ ID NO 12
<211> LENGTH: 3
<212> TYPE: PRT
<213> ORGANISM: Artificial Sequence
<220> FEATURE:
<223> OTHER INFORMATION: Description of Artificial Sequence: Peptidyl
      fragment

<400> SEQUENCE: 12

Ala Phe Met
  1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Peptidyl
      fragment

<400> SEQUENCE: 13

Ala Pro Ala Gly
  1
```

```
<210> SEQ ID NO 14
<211> LENGTH: 3
<212> TYPE: PRT
<213> ORGANISM: Artificial Sequence
<220> FEATURE:
<221> NAME/KEY: MOD_RES
<222> LOCATION: (3)
<223> OTHER INFORMATION: Xaa is homoserine lactone and/or homoserine
<223> OTHER INFORMATION: Description of Artificial Sequence: Peptidyl
      fragment

<400> SEQUENCE: 14

Ala Phe Xaa
  1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Peptidyl
      fragment

<400> SEQUENCE: 15

Leu Ala Phe Gly
  1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Peptidyl
      fragment

<400> SEQUENCE: 16

Ala Ala Gly Gly
  1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Peptidyl
      fragment

<400> SEQUENCE: 17

Ala Leu Ala Gly
  1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Peptidyl
      fragment

<400> SEQUENCE: 18

Ala Ala Pro Gly
  1

<210> SEQ ID NO 19
<211> LENGTH: 4
<212> TYPE: PRT
<213> ORGANISM: Artificial Sequence
```

-continued

```
<220> FEATURE:
<223> OTHER INFORMATION: Description of Artificial Sequence: Peptidyl
      fragment

<400> SEQUENCE: 19

Leu Ala Ala Gly
  1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Peptidyl
      fragment

<400> SEQUENCE: 20

Ala Ala Phe Gly
  1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Peptidyl
      fragment

<400> SEQUENCE: 21

Gln Ala Gln Gly
  1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Peptidyl
      fragment

<400> SEQUENCE: 22

His Ala Glu Gly
  1

<210> SEQ ID NO 23
<211> LENGTH: 33
<212> TYPE: PRT
<213> ORGANISM: Escherichia coli

<400> SEQUENCE: 23

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Ala Phe
             20                  25                  30

Ala

<210> SEQ ID NO 24
<211> LENGTH: 36
<212> TYPE: PRT
<213> ORGANISM: Escherichia coli

<400> SEQUENCE: 24

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Ala Phe
```

```
                        20                  25                  30

Ala His Ala Glu
            35

<210> SEQ ID NO 25
<211> LENGTH: 34
<212> TYPE: PRT
<213> ORGANISM: Escherichia coli

<400> SEQUENCE: 25

Glu Phe Glu Arg His Ala Glu Gly Thr Phe Thr Ser Asp Val Ser Ser
 1               5                  10                  15

Tyr Leu Glu Gly Gln Ala Ala Lys Glu Phe Ile Ala Trp Leu Val Lys
                20                  25                  30

Gly Arg
```